(12) United States Patent
Moon et al.

(10) Patent No.: US 12,170,576 B2
(45) Date of Patent: *Dec. 17, 2024

(54) METHOD FOR TRANSMITTING AND RECEIVING DATA CHANNEL BASED ON A PLURALITY OF SYMBOL SETS COMMUNICATION SYSTEM AND APPARATUS FOR THE SAME

(71) Applicant: ELECTRONICS AND TELECOMMUNICATIONS RESEARCH INSTITUTE, Daejeon (KR)

(72) Inventors: Sung Hyun Moon, Daejeon (KR); Cheul Soon Kim, Daejeon (KR); Seung Kwon Baek, Daejeon (KR); Gi Yoon Park, Daejeon (KR); Ok Sun Park, Daejeon (KR); Jae Su Song, Daejeon (KR)

(73) Assignee: ELECTRONICS AND TELECOMMUNICATIONS RESEARCH INSTITUTE, Daejeon (KR)

( * ) Notice: Subject to any disclaimer, the term of this patent is extended or adjusted under 35 U.S.C. 154(b) by 90 days.

This patent is subject to a terminal disclaimer.

(21) Appl. No.: 17/858,728

(22) Filed: Jul. 6, 2022

(65) Prior Publication Data

US 2022/0345257 A1    Oct. 27, 2022

Related U.S. Application Data

(63) Continuation of application No. 16/688,372, filed on Nov. 19, 2019, now Pat. No. 11,411,690.

(30) Foreign Application Priority Data

Nov. 21, 2018  (KR) .................. 10-2018-0144903
Dec. 12, 2018  (KR) .................. 10-2018-0160282
(Continued)

(51) Int. Cl.
*H04W 72/04*    (2023.01)
*A61B 17/00*    (2006.01)
(Continued)

(52) U.S. Cl.
CPC ............ *H04L 1/1896* (2013.01); *A61B 17/00* (2013.01); *A61H 23/006* (2013.01);
(Continued)

(58) Field of Classification Search
CPC . H04L 47/70; H04L 12/5695; H04L 27/2666; H04L 47/78; H04B 17/382;
(Continued)

(56) References Cited

U.S. PATENT DOCUMENTS 11,411,690 B2 *   8/2022   Moon ................. A61H 23/006
2015/0341960 A1   11/2015  Quan et al.
(Continued)

FOREIGN PATENT DOCUMENTS

WO    2015046830 A1    4/2015

OTHER PUBLICATIONS

3GPP, "TS 38.214 V15.3.0", Sep. 2018, pp. 1-96 (Year: 2018).*

*Primary Examiner* — Salvador E Rivas
(74) *Attorney, Agent, or Firm* — RABIN & BERDO, P.C.

(57) ABSTRACT

Disclosed are methods and apparatuses for transmitting and receiving data channels in a communication system. An operation method of a terminal in a communication system may comprise receiving, from a base station, resource allocation information of a plurality of physical uplink
(Continued)

shared channels (PUSCHs) used for repetitive transmission of a same transport block (TB); identifying a position of each of the plurality of PUSCHs in a time domain based on the resource allocation information; and repeatedly transmitting the same TB to the base station at the position of each of the plurality of PUSCHs. Therefore, performance of the communication system can be improved.

12 Claims, 9 Drawing Sheets

(30) Foreign Application Priority Data

| Apr. 17, 2019 | (KR) | .................. 10-2019-0045096 |
| Nov. 7, 2019 | (KR) | .................. 10-2019-0141479 |

(51) Int. Cl.

| *A61H 23/00* | (2006.01) |
| *H04B 17/382* | (2015.01) |
| *H04L 1/1812* | (2023.01) |
| *H04L 1/1867* | (2023.01) |
| *H04W 72/0446* | (2023.01) |
| *H04W 72/1273* | (2023.01) |
| *H04W 72/23* | (2023.01) |
| *H04W 72/231* | (2023.01) |
| *H04W 76/27* | (2018.01) |
| *H04J 11/00* | (2006.01) |
| *H04L 47/78* | (2022.01) |

(52) U.S. Cl.
CPC .......... *H04B 17/382* (2015.01); *H04L 1/1816* (2013.01); *H04W 72/04* (2013.01); *H04W 72/0446* (2013.01); *H04W 72/1273* (2013.01); *H04W 72/23* (2023.01); *H04W 72/231* (2023.01); *H04W 76/27* (2018.02); *A61B 2017/00367* (2013.01); *H04J 11/0079* (2013.01); *H04L 47/78* (2013.01)

(58) Field of Classification Search
CPC .. H04W 72/232; H04W 72/231; H04W 72/04
See application file for complete search history.

(56) References Cited

U.S. PATENT DOCUMENTS

| 2016/0156454 | A1 | 6/2016 | Khoryaev et al. |
| 2016/0234800 | A1 | 8/2016 | Jung et al. |
| 2017/0273113 | A1 | 9/2017 | Tirronen et al. |
| 2018/0167931 | A1 | 6/2018 | Papasakellariou |
| 2018/0199338 | A1 | 7/2018 | Nimbalker et al. |
| 2018/0278380 | A1 | 9/2018 | Kim et al. |
| 2018/0310257 | A1* | 10/2018 | Papasakellariou .... H04W 72/23 |
| 2019/0149365 | A1* | 5/2019 | Chatterjee ........... H04L 25/0226 |
| | | | 370/329 |
| 2020/0195387 | A1* | 6/2020 | Matsumura ........... H04L 5/0055 |
| 2020/0404656 | A1 | 12/2020 | Ji et al. |
| 2021/0235481 | A1* | 7/2021 | Takeda ................. H04L 5/0053 |
| 2021/0281458 | A1* | 9/2021 | Takeda ............. H04W 72/1268 |

* cited by examiner

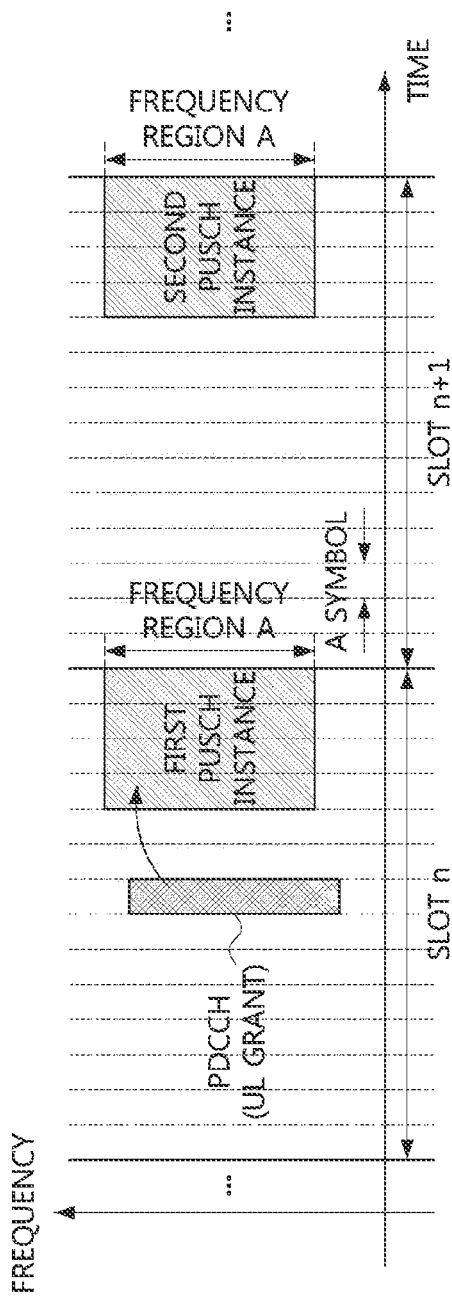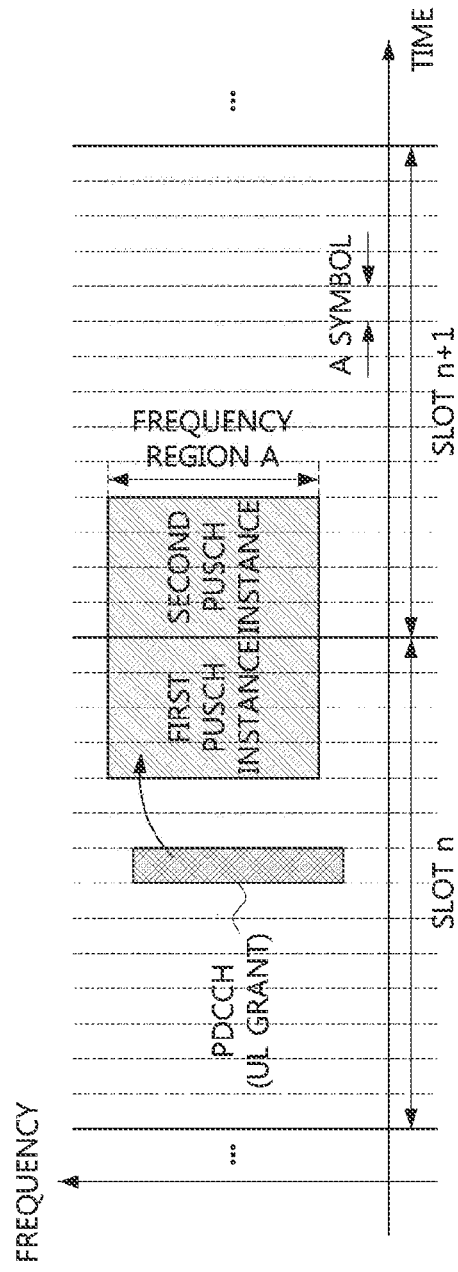
FIG. 3
FIG. 4A

METHOD FOR TRANSMITTING AND RECEIVING DATA CHANNEL BASED ON A PLURALITY OF SYMBOL SETS COMMUNICATION SYSTEM AND APPARATUS FOR THE SAME

CROSS-REFERENCE TO RELATED APPLICATIONS

This application is a continuation of U.S. application Ser. No. 16/688,372, filed on Nov. 19, 2019, which claims priority to Korean Patent Applications No. 10-2018-0144903 filed on Nov. 21, 2018, No. 10-2018-0160282 filed on Dec. 12, 2018, No. 10-2019-0045096 filed on Apr. 17, 2019, and No. 10-2019-0141479 filed on Nov. 7, 2019 with the Korean Intellectual Property Office (KIPO), the entire contents of which are hereby incorporated by reference.

BACKGROUND

1. Technical Field

The present disclosure relates generally to a technique for transmitting and receiving a data channel in a communication system, and more specifically, to a method for transmitting and receiving a data channel for a service requiring high reliability and low latency.

2. Related Art

The communication system (hereinafter, a new radio (NR) communication system) using a higher frequency band (e.g., a frequency band of 6 GHz or higher) than a frequency band (e.g., a frequency band lower below 6 GHz) of the long term evolution (LTE) (or, LTE-A) is being considered for processing of soaring wireless data. The NR communication system may support not only a frequency band below 6 GHz but also 6 GHz or higher frequency band, and may support various communication services and scenarios as compared to the LTE communication system. For example, usage scenarios of the NR communication system may include enhanced mobile broadband (eMBB), ultra-reliable low-latency communication (URLLC), massive machine type communication (mMTC), and the like.

In order to satisfy the URLLC requirements in the NR communication system, the same transport block (TB) may be repeatedly transmitted through a plurality of data channels (e.g., physical downlink shared channel (PDSCH), physical uplink shared channel (PUSCH), and physical sidelink shared channel (PSSCH)). For the repeated transmissions of the same TB, methods are needed for indicating the plurality of data channels.

SUMMARY

Accordingly, exemplary embodiments of the present disclosure provide a method for transmitting and receiving a data channel for a service requiring high reliability and low latency in a communication system.

According to an exemplary embodiment of the present disclosure, an operation method of a terminal in a communication system may comprise receiving, from a base station, resource allocation information of a plurality of physical uplink shared channels (PUSCHs) used for repetitive transmission of a same transport block (TB); identifying a position of each of the plurality of PUSCHs in a time domain based on the resource allocation information; and repeatedly transmitting the same TB to the base station at the position of each of the plurality of PUSCHs.

The resource allocation information may include information indicating a start symbol of each of the plurality of PUSCHs and information indicating a number of symbols constituting each of the plurality of PUSCHs in the time domain.

A start symbol of at least one PUSCH among the plurality of PUSCHs may be indicated by a symbol index or an offset between a previous slot boundary and the start symbol.

The resource allocation information may include information indicating an offset between a slot in which the resource allocation information is transmitted and a slot to which at least one PUSCH among the plurality of PUSCHs is allocated.

The resource allocation information may include information indicating a number of slots in which the plurality of PUSCHs are transmitted.

One PUSCH may be transmitted in one slot when the number of slots is equal to a number of the plurality of PUSCHs, and two or more PUSCHs may be transmitted in at least one slot when the number of slots is less than the number of the plurality of PUSCHs.

The slots in which the plurality of PUSCHs are transmitted may be contiguous in a time domain.

The resource allocation information may be received from the base station through downlink control information (DCI) or radio resource control (RRC) signaling.

The operation method may further comprise receiving resource allocation candidates of the plurality of PUSCHs from the base station through RRC signaling, wherein the resource allocation information indicates one resource allocation candidate among the resource allocation candidates, and the resource allocation information is received through DCI.

According to another exemplary embodiment of the present disclosure, an operation method of a base station in a communication system may comprise generating resource allocation information of a plurality of physical uplink shared channels (PUSCHs) used for repetitive transmission of a same transport block (TB); transmitting the resource allocation information to a terminal; and receiving the same TB from the terminal through the plurality of PUSCHs indicated by the resource allocation information.

The resource allocation information may include information indicating a start symbol of each of the plurality of PUSCHs, information indicating a number of consecutive symbol(s) constituting each of the plurality of PUSCHs in a time domain, information indicating an offset between a slot in which the resource allocation information is transmitted and a slot to which at least one PUSCH among the plurality of PUSCHs is allocated, and information indicating a number of slots through which the plurality of PUSCHs are transmitted.

A start symbol of at least one PUSCH among the plurality of PUSCHs may be indicated by a symbol index or an offset between a previous slot boundary and the start symbol.

One PUSCH may be received in one slot when the number of slots is equal to a number of the plurality of PUSCHs, and two or more PUSCHs may be received in at least one slot when the number of slots is less than the number of the plurality of PUSCHs.

The resource allocation information may be transmitted to the terminal through downlink control information (DCI) or radio resource control (RRC) signaling.

The operation method may further comprise transmitting resource allocation candidates of the plurality of PUSCHs to the terminal through RRC signaling, wherein the resource allocation information indicates one resource allocation candidate among the resource allocation candidates, and the resource allocation information is transmitted through DCI.

According to yet another exemplary embodiment of the present disclosure, a terminal in a communication system may comprise a processor and a memory storing at least one instruction executable by the processor, wherein the at least one instruction may configure the processor to receive, from a base station, resource allocation information of a plurality of physical uplink shared channels (PUSCHs) used for repetitive transmission of a same transport block (TB); identify a position of each of the plurality of PUSCHs in a time domain based on the resource allocation information; and repeatedly transmit the same TB to the base station at the position of each of the plurality of PUSCHs.

The resource allocation information may include information indicating a start symbol of each of the plurality of PUSCHs, information indicating a number of symbols constituting each of the plurality of PUSCHs in the time domain, information indicating an offset between a slot in which the resource allocation information is transmitted and a slot to which at least one PUSCH among the plurality of PUSCHs is allocated, and information indicating a number of slots through which the plurality of PUSCHs are transmitted.

A start symbol of at least one PUSCH among the plurality of PUSCHs may be indicated by a symbol index or an offset between a previous slot boundary and the start symbol.

One PUSCH may be transmitted in one slot when the number of slots is equal to a number of the plurality of PUSCHs, and two or more PUSCHs may be transmitted in at least one slot when the number of slots is less than the number of the plurality of PUSCHs.

The at least one instruction may further configure the processor to receive resource allocation candidates of the plurality of PUSCHs from the base station through RRC signaling, wherein the resource allocation information indicates one resource allocation candidate among the resource allocation candidates, and the resource allocation information is received through DCI.

According to the exemplary embodiments of the present disclosure, each of the base station and the terminal can repeatedly transmit the same transport block (TB) by using a plurality of data channels (e.g., physical downlink shared channel (PDSCH), physical uplink shared channel (PUSCH), physical sidelink shared channel (PSSCH)). To this end, the base station can transmit resource allocation information of the plurality of data channels to the terminal through radio resource control (RRC) signaling and/or downlink control information (DCI). In downlink communication, the terminal can receive the same TB from the base station through the plurality of data channels indicated by the resource allocation information. In uplink communication, the terminal can repeatedly transmit the same TB to the base station through the plurality of data channels indicated by the resource allocation information. Therefore, Ultra Reliable Low Latency Communication (URLLC) requirements can be met, and the performance of the communication system can be improved.

BRIEF DESCRIPTION OF DRAWINGS

Exemplary embodiments of the present disclosure will become more apparent by describing in detail exemplary embodiments of the present disclosure with reference to the accompanying drawings, in which:

FIG. 3 is a timing diagram illustrating a first exemplary embodiment of a method for repetitive transmission of a PUSCH in a communication system;

FIG. 4A is a timing diagram illustrating a second exemplary embodiment of a method for repetitive transmission of a PUSCH in a communication system;

Figure 1:
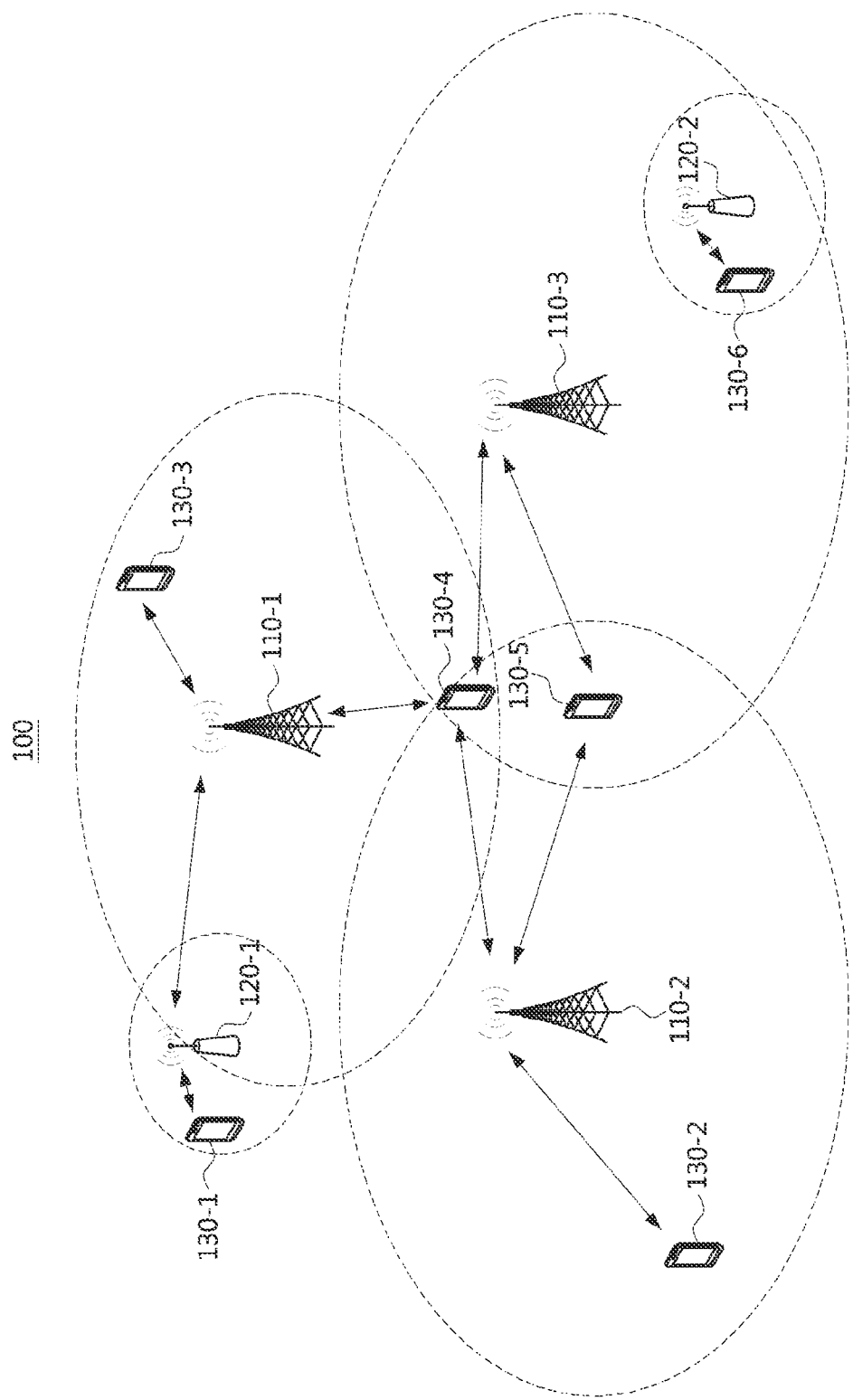
FIG. 1 is a conceptual diagram illustrating a first embodiment of a communication system.

It should be understood that the above-referenced drawings are not necessarily to scale, presenting a somewhat simplified representation of various preferred features illustrative of the basic principles of the disclosure. The specific design features of the present disclosure, including, for example, specific dimensions, orientations, locations, and shapes, will be determined in part by the particular intended application and use environment.

DETAILED DESCRIPTION OF THE EMBODIMENTS

While the present invention is susceptible to various modifications and alternative forms, specific embodiments are shown by way of example in the drawings and described in detail. It should be understood, however, that the description is not intended to limit the present invention to the specific embodiments, but, on the contrary, the present invention is to cover all modifications, equivalents, and alternatives that fall within the spirit and scope of the present invention.

Although the terms "first," "second," etc. may be used herein in reference to various elements, such elements should not be construed as limited by these terms. These terms are only used to distinguish one element from another. For example, a first element could be termed a second element, and a second element could be termed a first element, without departing from the scope of the present invention. The term "and/or" includes any and all combinations of one or more of the associated listed items.

It will be understood that when an element is referred to as being "connected" or "coupled" to another element, it can be directly connected or coupled to the other element or intervening elements may be present. In contrast, when an element is referred to as being "directly connected" or "directed coupled" to another element, there are no intervening elements.

The terminology used herein is for the purpose of describing particular embodiments only and is not intended to be limiting of embodiments of the present invention. As used herein, the singular forms "a," "an," and "the" are intended to include the plural forms as well, unless the context clearly indicates otherwise. It will be further understood that the terms "comprises," "comprising," "includes," and/or "including," when used herein, specify the presence of stated features, integers, steps, operations, elements, parts, and/or combinations thereof, but do not preclude the presence or addition of one or more other features, integers, steps, operations, elements, parts, and/or combinations thereof.

Unless otherwise defined, all terms (including technical and scientific terms) used herein have the same meaning as commonly understood by those of ordinary skill in the art to which the present invention pertains. It will be further understood that terms defined in commonly used dictionaries should be interpreted as having a meaning that is consistent with their meaning in the context of the related art and will not be interpreted in an idealized or overly formal sense unless expressly so defined herein.

Hereinafter, exemplary embodiments of the present invention will be described in greater detail with reference to the accompanying drawings. To facilitate overall understanding of the present invention, like numbers refer to like elements throughout the description of the drawings, and description of the same component will not be reiterated.

A communication system to which embodiments according to the present disclosure will be described. The communication system may be a 4G communication system (e.g., a long-term evolution (LTE) communication system, an LTE-A communication system), a 5G communication system (e.g. new radio (NR) communication system), or the like. The 4G communication system can support communication in a frequency band of 6 GHz or less, and the 5G communication system can support communication in a frequency band of 6 GHz or less as well as a frequency band of 6 GHz or more. The communication systems to which embodiments according to the present disclosure are applied are not restricted to what will be described below. That is, the embodiments according to the present disclosure may be applied to various communication systems. Here, the term 'communication system' may be used with the same meaning as the term 'communication network', 'LTE' may refer to '4G communication system', 'LTE communication system', or 'LTE-A communication system', and 'NR' may refer to '5G communication system' or 'NR communication system'.

FIG. 1 is a conceptual diagram illustrating a first embodiment of a communication system.

Referring to FIG. 1, a communication system 100 may comprise a plurality of communication nodes 110-1, 110-2, 110-3, 120-1, 120-2, 130-1, 130-2, 130-3, 130-4, 130-5, and 130-6. Also, the communication system 100 may further comprise a core network (e.g., a serving gateway (S-GW), a packet data network (PDN) gateway (P-GW), a mobility management entity (MME), and the like. When the communication system 100 is the 5G communication system (e.g., NR system), the core network may include an access and mobility management function (AMF), a user plane function (UPF), a session management function (SMF), and the like.

The plurality of communication nodes 110 to 130 may support communication protocols (e.g., LTE communication protocol, LTE-A communication protocol, NR communication protocol, or the like). The plurality of communication nodes 110 to 130 may support code division multiple access (CDMA) technology, wideband CDMA (WCDMA) technology, time division multiple access (TDMA) technology, frequency division multiple access (FDMA) technology, orthogonal frequency division multiplexing (OFDM) technology, filtered OFDM technology, cyclic prefix OFDM (CP-OFDM) technology, discrete Fourier transform-spread-OFDM (DFT-s-OFDM) technology, single carrier FDMA (SC-FDMA) technology, non-orthogonal multiple access (NOMA) technology, generalized frequency division multiplexing (GFDM) technology, filter band multi-carrier (FBMC) technology, universal filtered multi-carrier (UFMC) technology, space division multiple access (SDMA) technology, or the like. Each of the plurality of communication nodes may have the following structure.

Figure 2:
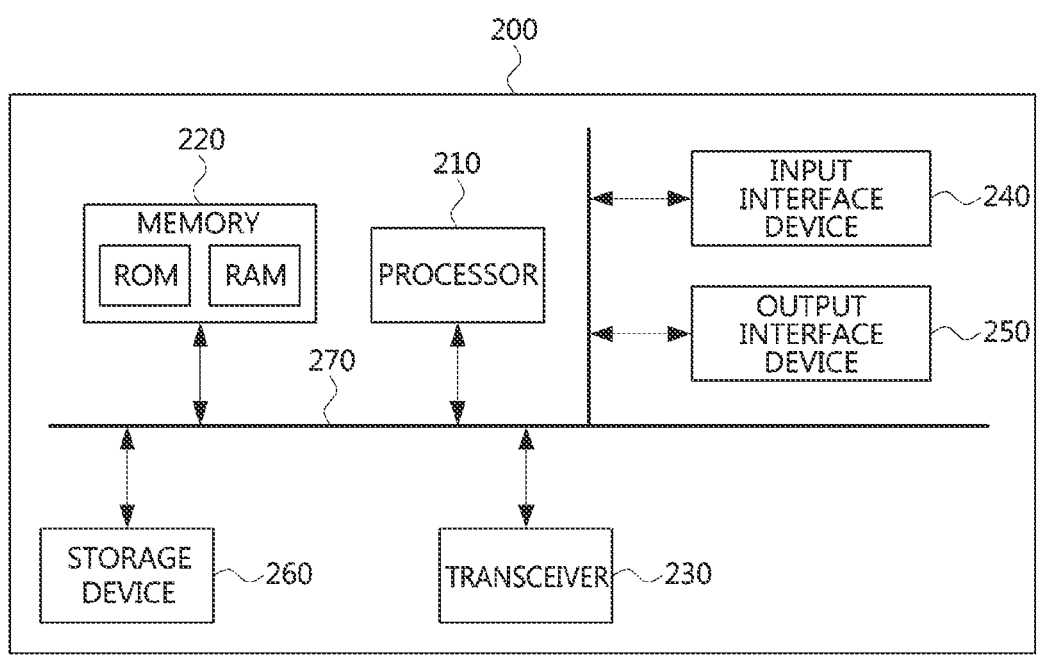
FIG. 2 is a block diagram illustrating a first embodiment of a communication node constituting a communication system.

FIG. 2 is a block diagram illustrating a first embodiment of a communication node constituting a communication system.

Referring to FIG. 2, a communication node 200 may comprise at least one processor 210, a memory 220, and a transceiver 230 connected to the network for performing communications. Also, the communication node 200 may further comprise an input interface device 240, an output interface device 250, a storage device 260, and the like. Each component included in the communication node 200 may communicate with each other as connected through a bus 270.

The processor 210 may execute a program stored in at least one of the memory 220 and the storage device 260. The processor 210 may refer to a central processing unit (CPU), a graphics processing unit (GPU), or a dedicated processor on which methods in accordance with embodiments of the present disclosure are performed. Each of the memory 220 and the storage device 260 may be constituted by at least one of a volatile storage medium and a non-volatile storage medium. For example, the memory 220 may comprise at least one of read-only memory (ROM) and random access memory (RAM).

Referring again to FIG. 1, the communication system 100 may comprise a plurality of base stations 110-1, 110-2, 110-3, 120-1, and 120-2, and a plurality of terminals 130-1, 130-2, 130-3, 130-4, 130-5, and 130-6. Each of the first base station 110-1, the second base station 110-2, and the third base station 110-3 may form a macro cell, and each of the fourth base station 120-1 and the fifth base station 120-2 may form a small cell. The fourth base station 120-1, the third terminal 130-3, and the fourth terminal 130-4 may belong to cell coverage of the first base station 110-1. Also, the second terminal 130-2, the fourth terminal 130-4, and the fifth terminal 130-5 may belong to cell coverage of the second base station 110-2. Also, the fifth base station 120-2, the fourth terminal 130-4, the fifth terminal 130-5, and the sixth terminal 130-6 may belong to cell coverage of the third base station 110-3. Also, the first terminal 130-1 may belong to cell coverage of the fourth base station 120-1, and the sixth terminal 130-6 may belong to cell coverage of the fifth base station 120-2.

Here, each of the plurality of base stations 110-1, 110-2, 110-3, 120-1 and 120-2 may refer to an NB (NodeB), an evolved NodeB (eNB), a gNB, an advanced base station (ABS), a high reliability base station (HR-BS), a base transceiver station (BTS), a radio base station, a radio transceiver, an access point, an access node, a radio access station (RAS), a mobile multihop relay base station (MMR-BS), a relay station (RS), an advanced relay station (ARS), a high reliability relay station (HR-RS), a home NodeB (HNB), a home eNodeB (HeNB), a roadside unit (RSU), a radio remote head (RRH), a transmission point (TP), a transmission and reception point (TRP), or the like.

Each of the plurality of terminals 130-1, 130-2, 130-3, 130-4, 130-5 and 130-6 may refer to a user equipment (UE), a terminal equipment (TE), an advanced mobile station (AMS), a high reliability-mobile station (HR-MS), a terminal, an access terminal, a mobile terminal, a station, a subscriber station, a mobile station, a mobile subscriber station, a node, a device, an on board unit (OBU), or the like.

Meanwhile, each of the plurality of base stations 110-1, 110-2, 110-3, 120-1, and 120-2 may operate in the same frequency band or in different frequency bands. The plurality of base stations 110-1, 110-2, 110-3, 120-1, and 120-2 may be connected to each other via an ideal backhaul or a non-ideal backhaul, and exchange information with each other via the ideal or non-ideal backhaul. Also, each of the plurality of base stations 110-1, 110-2, 110-3, 120-1, and 120-2 may be connected to the core network through the ideal or non-ideal backhaul. Each of the plurality of base stations 110-1, 110-2, 110-3, 120-1, and 120-2 may transmit a signal received from the core network to the corresponding terminal 130-1, 130-2, 130-3, 130-4, 130-5, or 130-6, and transmit a signal received from the corresponding terminal 130-1, 130-2, 130-3, 130-4, 130-5, or 130-6 to the core network.

Also, each of the plurality of base stations 110-1, 110-2, 110-3, 120-1, and 120-2 may support a multi-input multi-output (MIMO) transmission (e.g., a single-user MIMO (SU-MIMO), a multi-user MIMO (MU-MIMO), a massive MIMO, or the like), a coordinated multipoint (CoMP) transmission, a carrier aggregation (CA) transmission, a transmission in unlicensed band, a device-to-device (D2D) communications (or, proximity services (ProSe)), or the like. Here, each of the plurality of terminals 130-1, 130-2, 130-3, 130-4, 130-5, and 130-6 may perform operations corresponding to the operations of the plurality of base stations 110-1, 110-2, 110-3, 120-1, and 120-2 (i.e., the operations supported by the plurality of base stations 110-1, 110-2, 110-3, 120-1, and 120-2). For example, the second base station 110-2 may transmit a signal to the fourth terminal 130-4 in the SU-MIMO manner, and the fourth terminal 130-4 may receive the signal from the second base station 110-2 in the SU-MIMO manner. Alternatively, the second base station 110-2 may transmit a signal to the fourth terminal 130-4 and fifth terminal 130-5 in the MU-MIMO manner, and the fourth terminal 130-4 and fifth terminal 130-5 may receive the signal from the second base station 110-2 in the MU-MIMO manner.

The first base station 110-1, the second base station 110-2, and the third base station 110-3 may transmit a signal to the fourth terminal 130-4 in the CoMP transmission manner, and the fourth terminal 130-4 may receive the signal from the first base station 110-1, the second base station 110-2, and the third base station 110-3 in the CoMP manner. Also, each of the plurality of base stations 110-1, 110-2, 110-3, 120-1, and 120-2 may exchange signals with the corresponding terminals 130-1, 130-2, 130-3, 130-4, 130-5, or 130-6 which belongs to its cell coverage in the CA manner. Each of the base stations 110-1, 110-2, and 110-3 may control D2D communications between the fourth terminal 130-4 and the fifth terminal 130-5, and thus the fourth terminal 130-4 and the fifth terminal 130-5 may perform the D2D communications under control of the second base station 110-2 and the third base station 110-3.

Meanwhile, the communication system (e.g., NR communication system) may support one or more services among the enhanced mobile broadband (eMBB) service, the ultra-reliable and low-latency communication (URLLC) service, and the massive machine type communication (mMTC) service. Communication may be performed to satisfy technical requirements of the services in the communication system. In the URLLC service, the requirements of the transmission reliability may be $1\text{-}10^5$, and the requirement of the uplink and downlink user plane latency may be 0.5 ms.

Numerology applied to physical signals and channels in the communication system may be varied. In a communication system to which a cyclic prefix (CP) based OFDM waveform technique is applied, the numerology may include a subcarrier spacing and a CP length (or CP type). Table 1 may be a first embodiment of numerologies for the CP-based OFDM. The subcarrier spacings may have a relationship of a multiple of a power of two with each other, and the CP length may be scaled at the same rate as the OFDM symbol length. Depending on a frequency band in which the communication system operates, a part of the numerologies in Table 1 may be supported. When the subcarrier spacing is 60 kHz, an extended CP may be further supported.

TABLE 1

| Subcarrier Spacing | 15 kHz | 30 kHz | 60 kHz | 120 kHz | 240 kHz |
| --- | --- | --- | --- | --- | --- |
| OFDM symbol length (µs) | 66.7 | 33.3 | 16.7 | 8.3 | 4.2 |
| CP length (µs) | 4.76 | 2.38 | 1.19 | 0.60 | 0.30 |

In the following description, a frame structure in the communication system (e.g., NR communication system) will be described. In the time domain, a building block may be a subframe, a slot, and/or a minislot. The subframe may be used as a transmission unit, and the length of the subframe may have a fixed value (e.g., 1 ms) regardless of the subcarrier spacing. The slot may comprise 14 consecutive OFDM symbols. The length of the slot may be variable differently from the length of the subframe, and may be inversely proportional to the subcarrier spacing. The slot may be used as a scheduling unit and may be used as a configuration unit of scheduling and hybrid automatic repeat request (HARQ) timing.

The base station may schedule a data channel (e.g., physical downlink shared channel (PDSCH) or physical uplink shared channel (PUSCH)) using a part of the slot or the entire slot. Alternatively, the base station may schedule a data channel using a plurality of slots. The minislot may be used as a transmission unit, and the length of the minislot may be set shorter than the length of the slot. A slot having a length shorter than the length of the conventional slot may be referred to as a 'minislot' in the communication system. A physical downlink control channel (PDCCH) monitoring period and/or a duration of the data channel may be configured to be shorter than the conventional slot, such that minislot-based transmission can be supported.

The scalable numerology and/or minislot may be suitable for transmission of a short transmission time interval (TTI) for URLLC. For example, when a slot-based scheduling scheme is used, since the length of the slot is inversely proportional to the subcarrier spacing, the length of the TTI may be reduced by using a numerology having a relatively large subcarrier spacing (e.g., 60 kHz). In another example, when minislot-based scheduling scheme is used, the length of the TTI may be reduced by allocating a data channel with a relatively short duration (e.g., a data channel comprised of 2 symbols). In this case, for transmission of a control channel including scheduling information of the data channel, the PDCCH monitoring period of the terminal may be configured to be suitable for the short TTI.

In the frequency domain, a building block may be a physical resource block (PRB). One PRB may comprise 12 consecutive subcarriers regardless of the subcarrier spacing. Thus, a bandwidth occupied by one PRB may be proportional to the subcarrier spacing of the numerology. The PRB may be used as a frequency-domain resource allocation unit of the control channel and/or data channel. The minimum resource allocation unit of the downlink control channel may be a control channel element (CCE). One CCE may include one or more PRBs. The minimum resource allocation (e.g., bitmap-based resource allocation) unit of the data channel may be a resource block group (RBG). One RBG may include one or more PRBs.

A slot (e.g., slot format) may be composed of a combination of one or more of downlink duration, flexible duration or unknown duration (hereinafter collectively referred to as 'flexible duration'), and an uplink duration. Each of the downlink duration, the flexible duration, and the uplink duration may be comprised of one or more consecutive symbols. The flexible duration may be located between the downlink duration and the uplink duration, between a first downlink duration and a second downlink duration, or between a first uplink duration and a second uplink duration. When the flexible duration is inserted between the downlink duration and the uplink duration, the flexible duration may be used as a guard period. One slot may include a plurality of flexible durations. Alternatively, one slot may not include a flexible duration. The terminal may perform a predefined operation or an operation configured by the base station semi-statically or periodically (e.g., a PDCCH monitoring operation, a synchronization signal/physical broadcast channel (SS/PBCH) block reception and measurement operation, a channel state information-reference signal (CSI-RS) reception and measurement operation, a downlink semi-persistent scheduling (SPS) PDSCH reception operation, a sounding reference signal (SRS) transmission operation, a physical random access channel (PRACH) transmission operation, a periodically-configured PUCCH transmission operation, a PUSCH transmission operation according to a configured grant, or the like) in the corresponding flexible duration until the corresponding flexible duration is overridden to be a downlink duration or an uplink duration. Alternatively, the terminal may not perform any operation in the corresponding flexible duration until the corresponding flexible duration is overridden to be a downlink duration or an uplink duration.

The slot format may be configured semi-statically by higher layer signaling (e.g. radio resource control (RRC) signaling). Information indicating a semi-static slot format may be included in system information, and the semi-static slot format may be configured in a cell-specific manner. In addition, the slot format may be additionally configured for each terminal through UE-specific higher layer signaling (e.g., RRC signaling). The flexible duration of the slot format configured in the cell-specific manner may be overridden by the UE-specific higher layer signaling to a downlink duration or an uplink duration. Also, the slot format may be dynamically indicated by a slot format indicator (SFI) included in downlink control information (DCI).

The terminal may perform most of downlink and uplink operations in a bandwidth part. The bandwidth part may be defined as a set of consecutive PRBs in the frequency domain. Only one numerology may be used for transmission of a control channel or a data channel in one bandwidth part. The terminal performing an initial access procedure may obtain configuration information of an initial bandwidth part from the base station through system information. A terminal operating in an RRC connected state may obtain the configuration information of the bandwidth part from the base station through UE-specific higher layer signaling.

The configuration information of the bandwidth part may include a numerology (e.g., a subcarrier spacing and a CP length) applied to the bandwidth part. Also, the configuration information of the bandwidth part may further include information indicating a position of a starting PRB of the bandwidth part and information indicating the number of PRBs constituting the bandwidth part. At least one bandwidth part of the bandwidth part(s) configured to the terminal may be activated. For example, within one carrier, one uplink bandwidth part and one downlink bandwidth part may be activated respectively. In a time division duplex (TDD) based communication system, a pair of one uplink bandwidth part and one downlink bandwidth part may be activated. If a plurality of bandwidth parts are configured for the terminal within one carrier, the active bandwidth part of the terminal may be switched.

The minimum resource unit constituting the PDCCH may be a resource element group (REG). The REG may be composed of one PRB (e.g., 12 subcarriers) in the frequency domain and one OFDM symbol in the time domain. Thus, one REG may include 12 resource elements (REs). In the OFDM-based communication system, an RE may be a minimum physical resource unit composed of one subcarrier and one OFDM symbol. A demodulation reference signal (DMRS) for demodulating the PDCCH may be mapped to 3 REs among 12 REs constituting the REG, and control information (e.g., modulated DCI) may be mapped to the remaining 9 REs.

One PDCCH candidate may be composed of one CCE or aggregated CCEs. One CCE may be composed of a plurality of REGs. In the embodiments, a CCE aggregation level may be referred to as L, and the number of REGs constituting one CCE may be referred to as K. The communication system (e.g., NR communication system) may support 'K=6, L=1, 2, 4, 8 or 16'. The higher the CCE aggregation level, the more physical resources may be used for transmission of a PDCCH. In this case, by using a low code rate for the PDCCH transmission, the reception performance of the PDCCH can be improved.

A control resource set (CORESET) may be a resource region in which the terminal performs a blind decoding on PDCCHs. The CORESET may be composed of a plurality of REGs. The CORESET may consist of one or more PRBs in the frequency domain and one or more symbols (e.g., OFDM symbols) in the time domain. The symbols constituting one CORESET may be consecutive in the time domain. The PRBs constituting a single CORESET may be continuous or discontinuous in the frequency domain. One DCI (e.g., one PDCCH) may be transmitted within one CORESET or one search space logically associated with the CORESET. Multiple CORESETs may be configured with respect to a cell and a terminal, and the CORESETs may overlap each other.

The CORESET may be configured to the terminal by a PBCH (e.g., system information transmitted through the PBCH). The ID of the CORESET configured by the PBCH may be 0. That is, the CORESET configured by the PBCH may be referred to as a CORESET #0. A terminal operating in an RRC idle state may perform a monitoring operation in the CORESET #0 in order to receive a first PDCCH in the initial access procedure. Not only terminals operating in the RRC idle state but also terminals operating in the RRC connected state may perform monitoring operations in the CORESET #0. The CORESET may be configured to the terminal by other system information (e.g., system information block type 1 (SIB1)) other than the system information transmitted through the PBCH. For example, for reception of Msg2 and Msg4 in a random access procedure, the terminal may receive the SIB1 including the configuration information of the CORESET. Also, the CORESET may be configured to the terminal by UE-specific higher layer signaling (e.g., RRC signaling).

In each downlink bandwidth part, one or more CORESETs may be configured for the terminal. Here, a case that the CORESET is configured in the bandwidth part means that the CORESET is logically associated with the bandwidth part and the terminal monitors the corresponding CORESET in the bandwidth part. The initial downlink active bandwidth part may include the CORESET #0 and may be associated with the CORESET #0. The CORESET #0 having a quasi-co-location (QCL) relationship with an SS/PBCH block may be configured for the terminal in a primary cell (PCell), a secondary cell (SCell), and a primary secondary cell (PSCell). In the secondary cell (SCell), the CORESET #0 may not be configured for the terminal.

The terminal may receive a PDCCH using a blind decoding scheme. A search space may be a set of candidate resource regions through which a PDCCH can be transmitted. The terminal may perform a blind decoding on each of the PDCCH candidates within a search space which is predefined or configured by the base station. The terminal may determine whether a PDCCH is transmitted to itself by performing a cyclic redundancy check (CRC) on a blind decoding result. When it is determined that a PDCCH is a PDCCH for the terminal itself, the terminal may receive the PDCCH.

A PDCCH candidate constituting the search space may consist of CCEs selected by a predefined hash function within an occasion of the CORESET or the search space. The search space may be defined and configured for each CCE aggregation level. In this case, a set of search spaces for all CCE aggregation levels may be referred to as a 'search space set'. In the embodiments, 'search space' may mean 'search space set', and 'search space set' may mean 'search space'.

A search space set may be logically associated with a single CORESET. One CORESET may be logically associated with one or more search space sets. A common search space set configured through the PBCH may be used to monitor a DCI scheduling a PDSCH for transmission of the SIB1. The ID of the common search space set configured through the PBCH may be set to 0. That is, the common search space set configured through the PBCH may be defined as a type 0 PDCCH common search space set or a search space set #0. The search space set #0 may be logically associated with the CORESET #0.

The search space set may be classified into a common search space set and a UE-specific search space set. A common DCI may be transmitted in the common search space set, and a UE-specific DCI may be transmitted in the UE-specific search space set. Considering degree of freedom in scheduling and/or fallback transmission, UE-specific DCIs may also be transmitted in the common search space set. For example, the common DCI may include resource allocation information of a PDSCH for transmission of system information, paging, power control commands, slot format indicator (SFI), preemption indicator, and the like. The UE-specific DCI may include PDSCH resource allocation information, PUSCH resource allocation information, and the like. A plurality of DCI formats may be defined according to the payload and the size of the DCI, the type of radio network temporary identifier (RNTI), or the like.

In the exemplary embodiments, the common search space may be referred to as a 'CSS', and the common search space set may be referred to as a 'CSS set'. Also, in the exemplary embodiments, the UE-specific search space may be referred to as a 'USS', and the UE-specific search space set may be referred to as a 'USS set'.

Meanwhile, since a communication system (e.g., NR communication system) can support a wide frequency band of 0 to 100 GHz, a method of operating beams in a high frequency band may be different from that of a low frequency band. Since a single path loss due to a channel is relatively small in the low frequency band (e.g., the band below 6 GHz), the signal may be transmitted and received using a beam having a wide beamwidth. In particular, even when a control channel is transmitted using a single beam, the control channel may be transmitted throughout a cell or a sector. That is, the entire cell or the entire sector can be covered by a single beam.

On the other hand, since a signal path loss due to a channel is relatively large in the high frequency band (e.g., the band above 6 GHz), the signal may be transmitted in a beamforming scheme using a plurality of antennas. For extension of cell coverage or terminal coverage, not only data channels but also common signals and control channels may be transmitted in a beamforming scheme. In this case, when a beam having a narrow beamwidth is formed through a plurality of antennas, a signal may be transmitted several times using beams in different directions to cover the entire cell or the entire sector. The operation in which the beamformed signal is transmitted several times through different resources in the time domain may be referred to as a beam sweeping operation. A system for transmitting signals using beams having a narrow beamwidth may be referred to as a multi-beam system.

Beam management may be required in the multi-beam system. In this case, the terminal may measure quality of a beam by receiving a specific reference signal (e.g., reference signal (RS) for beam management or RS for beam failure detection), and report information indicating one or more beams of good quality to the base station. For example, the terminal may calculate a reference signal received power (RSRP) for each of the beams and report to the base station information indicating the best beam in terms of RSRP (e.g., beam quality information). The base station may determine a beam to be used for transmission of a physical signal or channel based on the beam quality information received from the terminal, and may configure one or more transmission configuration information (TCI) states for a physical channel (e.g., PDCCH and PDSCH) in the terminal.

The TCI state may include an ID of a reference signal having a QCL relationship with a DMRS of the physical channel to which the TCI is applied and/or a QCL type. The QCL may include a spatial QCL. A case that a spatial QCL for a channel and/or a reference signal is established may mean that the terminal can assume the same reception beam (e.g., analog reception beam), the same reception channel spatial correlation, and the like for the corresponding channel and/or reference signal. The reception beam and the reception channel spatial correlation may be referred to as a spatial reception (RX) parameter. In addition to the spatial QCL, channel characteristics such as delay spread, Doppler spread, Doppler shift, average gain, and average delay may be configured as a QCL by configuring a TCI state. In the embodiments, the QCL may refer to a general QCL or spatial QCL. In the NR communication system, the spatial QCL may correspond to QCL-TypeD.

Hereinafter, methods for transmitting and receiving data channels in the communication system will be described. Even when a method (e.g., transmission or reception of a signal) to be performed at a first communication node among communication nodes is described, a corresponding second communication node may perform a method (e.g., reception or transmission of the signal) corresponding to the method performed at the first communication node. That is, when an operation of a terminal is described, a corresponding base station may perform an operation corresponding to the operation of the terminal. Conversely, when an operation of the base station is described, the corresponding terminal may perform an operation corresponding to the operation of the base station.

The exemplary embodiments below relate to methods for repetitive transmission of a data channel to ensure the requirements of the URLLC service (e.g., high transmission reliability). The following exemplary embodiments may be applied to various wireless communication systems as well as the NR communication system.

A plurality of HARQ processes may be performed in a communication system. For example, up to 16 HARQ processes may be performed for each of uplink and downlink in the NR communication system. The HARQ process(es) may be managed by an HARQ entity. When a plurality of carriers are aggregated for a terminal, the HARQ entity may be operated for each carrier, and the plurality of HARQ processes may be performed for each carrier.

Data that the base station or the terminal desires to transmit may be managed in units of a transport block (TB) or a medium access control (MAC) protocol data unit (PDU) by each HARQ process. In downlink communication, a TB or MAC PDU may be transmitted from the base station to the terminal through a data channel. In this case, the TB or MAC PDU may include a downlink shared channel (DL-SCH) and/or a MAC control element (CE). In uplink communication, a TB or MAC PDU may be transmitted from the terminal to the base station through a data channel. In this case, the TB or MAC PDU may include an uplink shared channel (UL-SCH), a MAC CE, and/or physical layer control information (e.g., uplink control information (UCI)). The data channel may include a downlink data channel (e.g., physical downlink shared channel (PDSCH)), an uplink data channel (e.g., physical uplink shared channel (PUSCH)), and a sidelink data channel (e.g., physical sidelink shared channel (PSSCH)).

When a dynamic scheduling scheme is used, scheduling information of a data channel may be included in a DCI. The DCI may be transmitted to the terminal through a PDCCH. When a semi-static scheduling scheme is used, scheduling information of a data channel may be configured to the terminal through RRC signaling. The scheduling information of the data channel may be transmitted to the terminal using at least one of RRC signaling, DCI, and a MAC CE. For example, a part of the scheduling information (e.g., transmission configuration information (TCI) state information) of the data channel may be indicated to the terminal through a MAC CE.

[Repetitive Transmission Method of Data Channel]

The data channels corresponding to the same HARQ process may be repeatedly transmitted. In this case, one transmission in the repeated transmission procedure of the data channel may be referred to as an 'instance'. For example, each PDSCH transmission may be referred to as a 'PDSCH instance' when the PDSCH is repeatedly transmitted, each PUSCH transmission may be referred to as a 'PUSCH instance' when the PUSCH is repeatedly transmitted, and each PSSCH transmission may be referred to as a 'PSSCH instance' when the PSSCH is repeatedly transmitted. Each 'instance' of a data channel may mean each transmission occasion of the data channel. Each 'instance' of a data channel may also be referred to as the data channel. For example, a case that a PUSCH is transmitted in a slot may mean that a PUSCH instance is transmitted in the corresponding slot.

The instances constituting repetitive transmission of the data channel may correspond to the same HARQ process and may include coded data for the same TB(s). In the following exemplary embodiments, 'repetitive transmission of a data channel' may mean 'repetitive transmission for the same HARQ process and the same TB(s)'. The following exemplary embodiments may be applied to other data channels (e.g., PSSCH) as well as PDSCH and PUSCH. For example, the following exemplary embodiments defining a PUSCH transmission method may be applied also to PDSCH and PSSCH transmission. In addition, the following exemplary embodiments defining the PUSCH transmission method relate to a communication method between a base station and a terminal, but the PSSCH transmission method to which the following exemplary embodiments are applied may be understood as a communication method between a terminal and another terminal.

The data channel (e.g., PDSCH, PUSCH, or PSSCH) may be repeatedly transmitted in a plurality of slots. There may be one data channel instance in each slot, and time and frequency resources for the data channel instance may be equally allocated in each slot. Each data channel instance may be mapped to contiguous symbol(s) in the time domain.

FIG. 3 is a timing diagram illustrating a first exemplary embodiment of a method for repetitive transmission of a PUSCH in a communication system.

Referring to FIG. 3, two consecutive slots may be aggregated, and the terminal may transmit a PUSCH in each slot. For example, the terminal may transmit the first PUSCH instance to the base station through a slot n, and may transmit the second PUSCH instance to the base station through a slot n+1. The time resources (e.g., eleventh to fourteenth symbols) allocated for the first PUSCH instance in the slot n may be the same as the time resources (e.g., eleventh to fourteenth symbols) allocated for the second PUSCH instance in the slot n+1. The frequency resources allocated for the first PUSCH instance in the slot n (e.g., frequency region A) may be the same as the frequency resources allocated for the second PUSCH instance in the slot n+1 (e.g., frequency region A).

Time and frequency domain resource allocation information of the PUSCH instance may be indicated to the terminal through an uplink (UL) grant transmitted through a PDCCH. The time and frequency domain resource allocation information indicated through the uplink grant may be one of resource allocation candidate(s) preconfigured to the terminal by RRC signaling. The uplink grant in the NR communication system may be defined as a DCI format 0_x (x=0, 1, 2, ... ). Here, it may be assumed that the terminal has a capability for transmitting a PUSCH after two symbols from a reception completion time of the uplink grant.

In addition to the same resource allocation information, the same scheduling (e.g., modulation and coding scheme (MCS), number of transmission layers, etc.) may be applied to the PUSCH instances. When PUSCH repetitive transmission is applied, the number of transmission layers may be limited to one. The redundancy version (RV) applied to each of the PUSCH instances may be identical or different. When a different RV is applied to each of the PUSCH instances, error correction capability by channel coding may be improved.

Meanwhile, in a communication system supporting the URLLC services, high transmission reliability and low latency can be guaranteed. Thus, sufficient time-frequency resources may be allocated for the control and/or data channel. Also, a time required for transmission in a wireless section may be short enough. In order to satisfy the URLLC requirements in the exemplary embodiment shown in FIG. 3, it may be assumed that at least eight symbols are allocated for the PUSCH, and the transmission timing of the uplink grant and the transmission start timing of the PUSCH in the slot n may be the earliest timing that the base station can schedule on the basis of the dynamic grant. In this case, since four uplink symbols are available for PUSCH transmission in the slot n, the base station may repeatedly transmit the PUSCH of the same TB in the slot n+1. That is, the base station may allocate additional symbols (e.g., four symbols) to the slot n+1 for the PUSCH transmission. However, since the positions (e.g., eleventh to fourteenth) of the symbols where the PUSCH instances are transmitted in the respective slots are the same, a transmission delay of the PUSCH may increase.

Figure 4B:
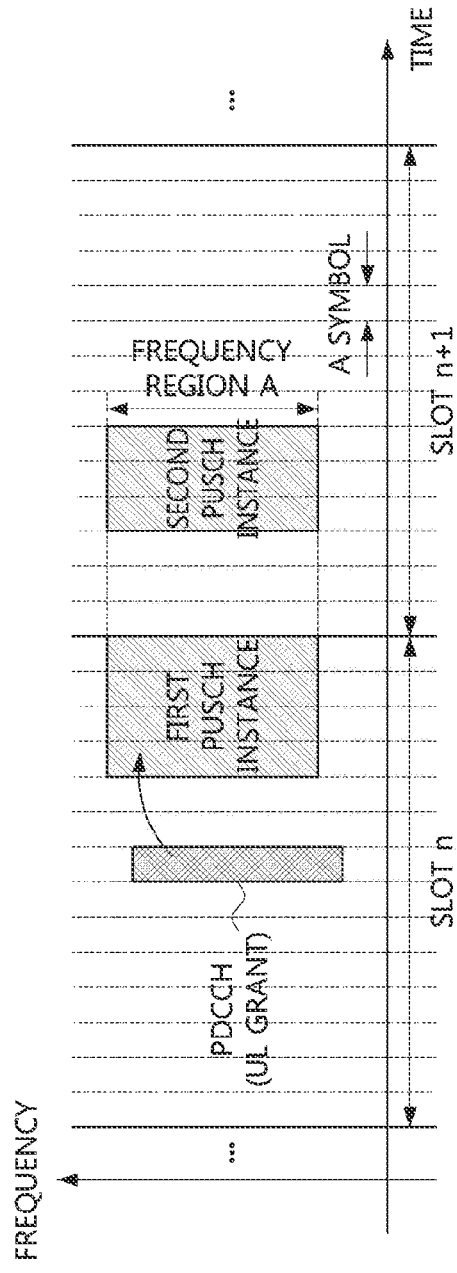
FIG. 4B is a timing diagram illustrating a third exemplary embodiment of a method for repetitive transmission of a PUSCH in a communication system.

FIG. 4A is a timing diagram illustrating a second exemplary embodiment of a method for repetitive transmission of a PUSCH in a communication system, and FIG. 4B is a timing diagram illustrating a third exemplary embodiment of a method for repetitive transmission of a PUSCH in a communication system.

As shown in FIGS. 4A and 4B, the position of time resources allocated for the first PUSCH instance in the slot n may be different from the position of time resources allocated for the second PUSCH instance in the slot n+1. In the exemplary embodiment shown in FIG. 4A, the first to fourth symbols of the slot n+1 may be allocated for the second PUSCH instance, and in the exemplary embodiment shown in FIG. 4B, the fourth to sixth symbols of the slot n+1 may be allocated for the second PUSCH instance.

The amount of resources used for transmission of the same TB in the exemplary embodiment shown in FIG. 4A may be the same as the amount of resources used for transmission of the same TB in the exemplary embodiment shown in FIG. 3. In the exemplary embodiment shown in FIG. 4A, a transmission completion time point of the same TB may be earlier by 10 symbols than the transmission completion time point of the same TB in the exemplary embodiment shown in FIG. 3. The amount of resources used for transmission of the same TB in the exemplary embodiment shown in FIG. 4B may be less than the amount of resources used for transmission of the same TB in the exemplary embodiment shown in FIG. 3. In the exemplary embodiment shown in FIG. 4B, a transmission completion time point of the same TB may be earlier by 7 symbols than the transmission completion time point of the same TB in the exemplary embodiment shown in FIG. 3.

Depending on a slot format configuration, uplink signal/channel configuration, and the like, a duration of symbols in which PUSCH can be transmitted in each slot may be different. Thus, as in the exemplary embodiments shown in FIGS. 4A and 4B, if the relative in-slot positions of the time resources and/or the numbers of symbols allocated for PUSCH instances are different, the transmission latency may be reduced and the transmission reliability may be improved. The method shown in FIG. 4A and/or FIG. 4B may be referred to as 'Method 100'. In the following exemplary embodiments, the number of repetitive transmissions of a data channel (e.g., PDSCH, PUSCH, or PSSCH) for the same TB may be defined as K. For example, K may correspond to the number of PUSCH instances scheduled by one DCI (e.g., uplink grant).

As specific methods of Method 100, 'Method 110' and 'Method 120' may be considered. In Method 110, a plurality of data channel instances may be regarded as one data channel (e.g., PDSCH, PUSCH, or PSSCH), and resource allocation information for one data channel may be configured. For example, the base station may inform the terminal of time domain resource allocation information for one PUSCH. The time domain resource allocation information for a PUSCH may include at least one of information indicating a start slot of the PUSCH (e.g., a slot offset between a reception time point (e.g., reception completion time point) of a PDCCH including an uplink grant and a transmission start time point of the PUSCH), information indicating a start symbol of the PUSCH, and information indicating a duration of the PUSCH (e.g., information indicating the number of consecutive symbols constituting the PUSCH). In addition, the time domain resource allocation information for one PUSCH may further include information (e.g., K) indicating the number of repetitive transmissions of the PUSCH.

The start symbol and the duration of the PUSCH may be represented by a single value (e.g., a start and length indicator value (SLIV)). When the index of the start symbol of the PUSCH is S and the duration of the PUSCH is L, the SLIV may be defined as in Equation 1 below. The index of the s-th symbol in the slot may be 's−1'. For example, the index of the eleventh symbol in the slot may be 10. In the NR communication system, '0≤S≤13' may be defined when a normal cyclic prefix (CP) is used, and '0≤S≤11' may be defined when an extended CP is used.

If $(L-1) \leq 7$, then $$SLIV = 14 \times (L-1) + S$$

Else $$SLIV = 14 \times (14-L+1) + (14-1-S)$$

Where $0 < L \leq 14-S$      [Equation 1]

In addition, the time domain resource allocation information for the PUSCH may further include information indicating a PUSCH mapping type. The PUSCH mapping type may indicate type A or type B. The terminal may identify the PUSCH mapping type by receiving the time domain resource allocation information from the base station. When the PUSCH mapping type A is applied in the communication system, the position of the first symbol of the DM-RS for demodulating the PUSCH may be semi-statically configured by RRC signaling (e.g., master information block (MIB) or cell-specific RRC signaling). Here, the position of the first symbol of the DM-RS may be configured based on a slot boundary as a reference time point. When the PUSCH mapping type B is applied in the communication system, the position of the first symbol of the DM-RS for demodulating the PUSCH may generally be the start symbol of the PUSCH. Alternatively, exceptionally, the position of the first symbol of the DM-RS may be another symbol except the start symbol of the PUSCH.

The valid ranges of S and L according to the PUSCH mapping type and the CP type may follow Table 2. Alternatively, the valid ranges of S and L may be extended. For example, if a sum of S and L exceeds 14, the corresponding values of S and L may be defined. The time domain resource allocation information of PDSCH may be configured the same as or similar to the above-described time domain resource allocation information of PUSCH.

TABLE 2

| PUSCH mapping type | Normal CP | | | Extended CP | | |
|---|---|---|---|---|---|---|
| | S | L | S + L | S | L | S + L |
| Type A | 0 | {4, . . . , 14} | {4, . . . , 14} | 0 | {4, . . . , 12} | {4, . . . , 12} |
| Type B | {0, . . . , 13} | {1, . . . , 14} | {1, . . . , 14} | {0, . . . , 12} | {1, . . . , 12} | {1, . . . , 12} |

Meanwhile, the start symbol S of the PUSCH may be represented by a symbol offset from a PDCCH scheduling the PUSCH. When the PDCCH occupies a plurality of symbols, the symbol offset may be defined based on one symbol among the plurality of symbols. For example, S may be defined as an offset between the start symbol or end symbol of the PDCCH and the start symbol of the PUSCH. In the exemplary embodiments shown in FIGS. 4A and 4B, S may be 3.

The exemplary embodiments shown in FIGS. 4A and 4B may be performed by Method 110. In the embodiment illustrated in FIG. 4A, when Method 110 is applied, the time domain resource allocation information for one PUSCH may include at least one of information indicating that a start slot of the PUSCH is n, information indicating that a slot offset between a PDCCH including an uplink grant and the PUSCH is 0, and information indicating that (S, L) is (10, 8). Each of S and L may be transmitted to the terminal. Alternatively, S and L may be transmitted to the terminal in the SLIV form. The above-described signaling methods for S and L may be equally applied in the following exemplary embodiments.

In the embodiment illustrated in FIG. 4A, when Method 110 is applied, the time domain resource allocation information for one PUSCH may include at least one of information indicating that a start slot of the PUSCH is n, information indicating that a slot offset between a PDCCH including an uplink grant and the PUSCH is 0, and information indicating that (S, L) is (10, 7).

In addition, when Method 110 is applied, even though the PUSCH is actually mapped to a plurality of slots, the base station may configure the number of slots aggregated for PUSCH transmission or a parameter (e.g., the number of PUSCH instances, K, aggregation factor, etc.) corresponding to the number of slots to be 1, and inform the configured value to the terminal. In the following exemplary embodiments, 'the number of slots aggregated for PUSCH transmission', 'the number of PUSCH instances', K, and 'aggregation factor' may be collectively referred to as 'the number of slots aggregated for PUSCH transmission'. The aggregation factor may be aggregationFactorUL which is an RRC parameter in uplink communication. The aggregation factor may be aggregationFactorDL which is an RRC parameter in downlink communication.

In the exemplary embodiments shown in FIGS. 4A and 4B, even when two PUSCH instances are scheduled in two consecutive slots from a terminal perspective, the base station may inform the terminal of time domain resource allocation information for one PUSCH. Also, the base station may transmit an RRC parameter (e.g., aggregationFactorUL) and/or a DCI indicating that the number of slots aggregated for PUSCH transmission is 1 to the terminal. The above-described time domain resource allocation information may be configured (e.g., indicated) to the terminal through DCI and/or RRC signaling.

When D valid symbol(s) in which the first PUSCH instance can be transmitted is defined as a 'first valid symbol set', L may be less than or equal to D in Method 110. In this case, the terminal may transmit the PUSCH using L symbols from the first symbol among the D valid symbols. In contrast, L may exceed D in Method 110. In this case, the terminal may transmit the first PUSCH instance using D valid symbols from the start slot of the PUSCH. The terminal may transmit PUSCH data corresponding to the remaining (L-D) symbols in valid symbol(s) of the next (or subsequent) slot(s). In the exemplary embodiments shown in FIGS. 4A and 4B, the first valid symbol set may be the eleventh to fourteenth symbols of the slot n. In this case, the first valid symbol set may include the start symbol of the PUSCH to the end symbol of the slot. All symbols from the start symbol of the PUSCH to the end symbol of the slot may not be downlink symbols. Here, a transmission direction (e.g., uplink or downlink) of a symbol may be determined according to a semi-static slot format configuration scheme.

Alternatively, a transmission direction of a symbol may be determined by a combination of a semi-static slot format configuration scheme and a dynamic slot format indication scheme. A dynamic slot format may include slot formats (e.g., SFI #46 to #55) in which at least one downlink symbol exists after flexible symbols or uplink symbols within one slot. In this case, the first valid symbol set may be a set of uplink symbol(s) and flexible symbol(s) consecutive from the start symbol of the PUSCH. If there is another continuous uplink and/or flexible duration even after the first valid symbol set in the start slot of the PUSCH, the terminal may transmit the PUSCH data corresponding to the remaining (L-D) symbols in the continuous uplink and/or flexible duration within an allowable range. That is, the terminal may transmit a plurality of PUSCH instances in one slot.

A valid symbol set (e.g., valid symbol(s) after the first valid symbol set in the start slot of the PUSCH and/or valid symbol(s) in the next slot(s)) for transmitting the remaining (L-D) symbols may be determined according to a slot format configuration scheme. For example, the valid symbol set in the next slot may be one or more of the flexible symbol(s) and uplink symbol(s) configured by the semi-static slot format configuration scheme. The terminal may transmit the next PUSCH instance using consecutive symbol(s) from the first symbol in the next valid symbol set. This may be referred to as 'Method 111'.

In the exemplary embodiment shown in FIG. 4A, when the slot n+1 is an uplink slot, all symbols of the slot n+1 may be valid symbols. Accordingly, the terminal may transmit the second PUSCH instance in four symbols (e.g., first to fourth symbols) consecutive from the first symbol in the slot n+1. In the exemplary embodiment shown in FIG. 4B, the first to third symbols of the slot n+1 may be downlink symbols, the fourth to fifth symbols of the slot n+1 may be flexible symbols, and the remaining symbols (e.g., sixth to fourteenth symbols) of the slot n+1 may be uplink symbols. In this case, the fourth to fourteenth symbols of the slot n+1 may be valid symbols. Accordingly, the terminal may transmit the second PUSCH instance in the fourth to sixth symbols of the slot n+1. Method 111 may have excellent performance in terms of transmission latency of the PUSCH, but according to Method 111, scheduling flexibility may be reduced.

Figure 5A:
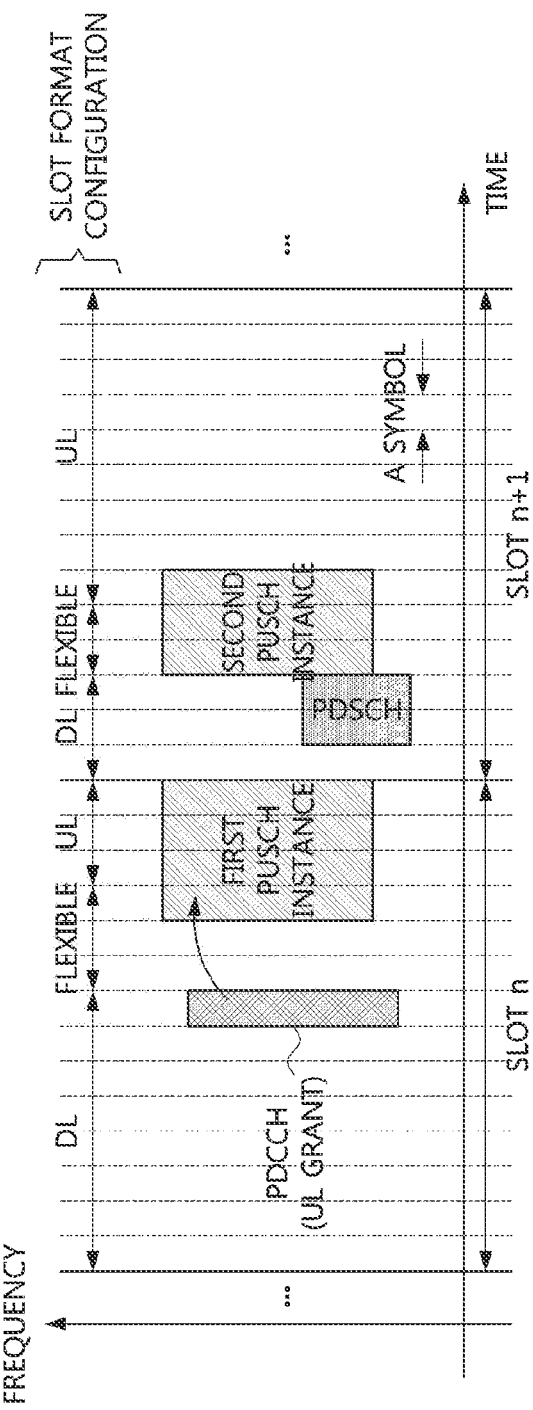
FIG. 5A is a timing diagram illustrating a fourth exemplary embodiment of a method for repetitive transmission of a PUSCH in a communication system.

FIG. 5A is a timing diagram illustrating a fourth exemplary embodiment of a method for repetitive transmission of a PUSCH in a communication system. The PUSCH scheduling scheme in FIG. 5A may be the same as the PUSCH scheduling scheme in FIG. 4B.

Referring to FIG. 5A, the first to third symbols of the slot n+1 may be downlink symbols, the fourth to fifth symbols of the slot n+1 may be flexible symbols, and the remaining symbols (e.g., sixth to fourteenth symbols) of the slot n+1 may be uplink symbols. According to Method 111, the second PUSCH instance may be transmitted in the fourth to sixth symbols of the slot n+1. In this case, a PDSCH may be scheduled in the second to third symbols of the slot n+1. When the PDSCH and the PUSCH are scheduled for the same terminal in the slot n+1, the terminal may not perform one of the reception operation of the PDSCH and the transmission operation of the PUSCH.

In order to resolve this problem, the terminal may regard the scheduling in which the downlink transmission and the uplink transmission overlap as an error, and may not expect the downlink transmission to overlap with the uplink transmission. Alternatively, when the downlink transmission and the uplink transmission overlap, the terminal may consider that a transmission scheduled first among the downlink transmission and the uplink transmission is valid or, conversely, that a late scheduled transmission is valid. Alternatively, the terminal may defer the start time of the next PUSCH instance(s) (e.g., second PUSCH instance). This may be referred to as 'Method 112'.

In addition, the terminal may determine the start symbol of the second PUSCH instance as a later symbol among the start symbol according to Method 111 and a symbol after a predetermined time from the reception completion time of the downlink channel (e.g., PDSCH), and may transmit the next PUSCH instance(s) (e.g., second PUSCH) from the determined symbol. This may be referred to as 'Method 113'. The predetermined time may be configured in unit of symbol(s). The base station may inform the terminal of the predetermined time.

On the other hand, when the receiving terminal of the PDSCH and the transmitting terminal of the PUSCH are different in the slot n+1, the second PUSCH instance may act as interference to the PDSCH. In order to allow scheduling of the PDSCH and to prevent interference between the PDSCH and the second PUSCH instance, Method 112 may be used.

Figure 5B:
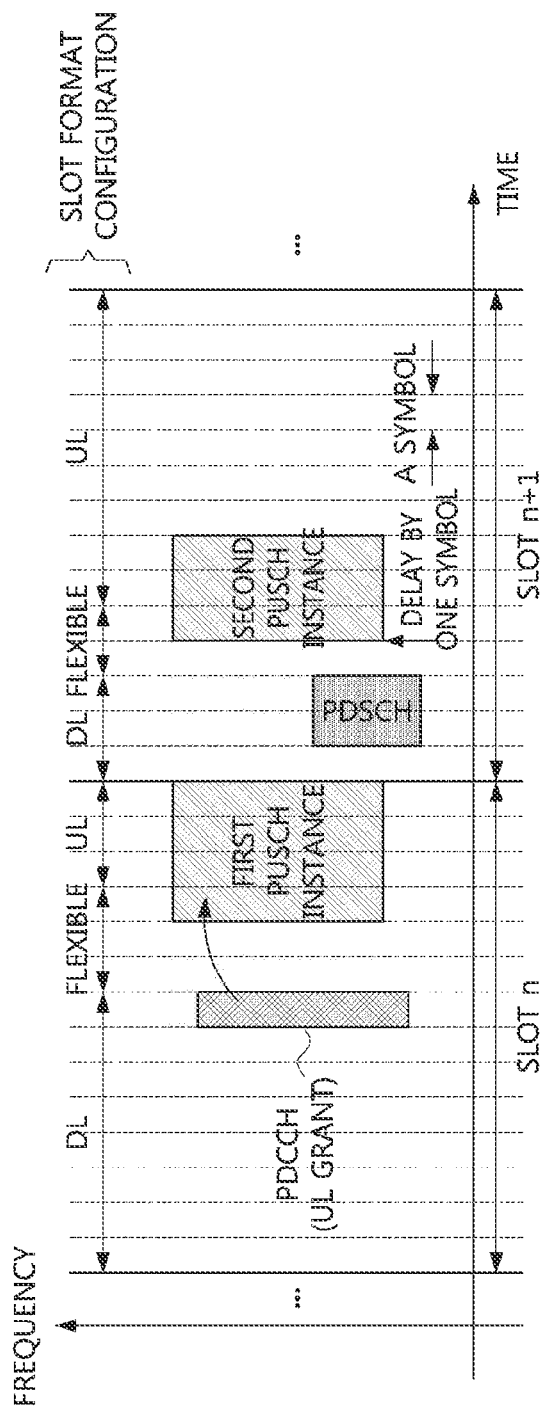
FIG. 5B is a timing diagram illustrating a fifth exemplary embodiment of a method for repetitive transmission of a PUSCH in a communication system.

FIG. 5B is a timing diagram illustrating a fifth exemplary embodiment of a method for repetitive transmission of a PUSCH in a communication system. For example, FIG. 5B illustrates a repetitive transmission method of a PUSCH according to Method 112 or Method 113.

Referring to FIG. 5B, the terminal may delay and transmit the second PUSCH instance by one symbol. The time offset for Method 112 or Method 113 may be configured semi-statically by RRC signaling. Alternatively, the time offset may be dynamically configured by DCI (e.g., uplink grant scheduling the PUSCH). Alternatively, the time offset may be configured by a combination of RRC signaling and DCI.

Since the number of symbols required for switching from the downlink communication to the uplink communication may vary according to a frequency band and a numerology, the time offset may be configured differently according to the frequency band and/or the numerology. The time offset may be configured for each carrier or bandwidth part (BWP). The time offset for repetitive PUSCH transmission according to a configured grant may be separately configured. When the number of repeated PUSCH instances is 3 or more, the time offset may be applied to the remaining PUSCH instances except the first PUSCH instance. The same time offset may be applied to a plurality of PUSCH instances.

Method 112 or Method 113 may be applied not only to the above-described exemplary embodiments but also to an exemplary embodiment in which symbol positions or start symbol positions of some PUSCH instances constituting the PUSCH repetitive transmission are determined by an implicit scheme. Method 110 may be one exemplary embodiment of the PUSCH repetitive transmission method, and Method 111 may be one exemplary embodiment in which the position of the start symbol of the PUSCH instance is implicitly determined.

Since the signaling scheme for the existing single slot based PUSCH scheduling is reused in Method 110, overhead of RRC signaling and/or DCI may be maintained. Or, the overhead of RRC signaling and/or DCI may increase by a minimum. However, various slot formats may be supported in a TDD band, and various configurations of uplink signals and channels (e.g., PUSCH, physical uplink control channel (PUCCH), SRS, PRACH, and the like) of the same terminal or different terminals may exist. In such environment, it may be difficult to generalize valid symbol determination rules considering multiplexing.

Thus, only with the existing signaling schemes or some improved methods (e.g., Method 112, Method 113, and the like), it may be difficult for the base station to schedule PUSCH instances in desired slot and symbol positions. 'Method 120' below may be used to resolve this problem.

In Method 120, the base station may inform the terminal of resource allocation information for a plurality of PUSCH instances. For example, the base station may signal time domain resource allocation information for each PUSCH instance to the terminal. In this case, unlike Method 110, the base station may inform the terminal of information indicating the number of slots aggregated for the PUSCH transmission. For example, in the exemplary embodiments shown in FIGS. 4A and 4B, when two PUSCH instances are scheduled in two consecutive slots, the base station may transmit to the terminal an RRC parameter (e.g., aggregationFactorUL) or a DCI indicating that the number of slots aggregated for the PUSCH transmission is 2.

In Method 120, a part of the time domain resource allocation information may be configured (e.g., indicated) to the terminal for each PUSCH instance. For example, the base station may inform the terminal of a start symbol and a length L of each of the PUSCH instances. This may be referred to as 'Method 121'. As an index of the start symbol of the PUSCH instance, a symbol index S in a slot may be used. The symbol index S may indicate a relative distance from a previous slot boundary to the start time of the PUSCH instance. This may be referred to as 'Method 122'.

The exemplary embodiments shown in FIGS. 4A and 4B may be performed by Method 121 or Method 122. When Method 122 is applied to the exemplary embodiment shown in FIG. 4A, the base station may inform the terminal of (S, L)=(10, 4) configured for the first PUSCH instance, and may inform the terminal of (S, L)=(0, 4) configured for the second PUSCH instance. When Method 122 is applied to the exemplary embodiment shown in FIG. 4B, the base station may inform the terminal of (S, L)=(10, 4) configured for the first PUSCH instance, and may inform the terminal of (S, L)=(3, 3) configured for the second PUSCH instance.

Method 120 and the detailed methods of Method 120 may be used for slot-based PUSCH repetitive transmission. For example, in Method 120 to Method 122, a plurality of PUSCH instances may be mapped to different slots. In this case, the number of slots aggregated for PUSCH transmission may be equal to the number of PUSCH instances. Accordingly, the terminal may receive information indicating the number of slots or the number of PUSCH instances aggregated for PUSCH transmission from the base station. The information indicating the number of slots aggregated for PUSCH transmission may be transmitted using the above-described signaling scheme.

Figure 6:
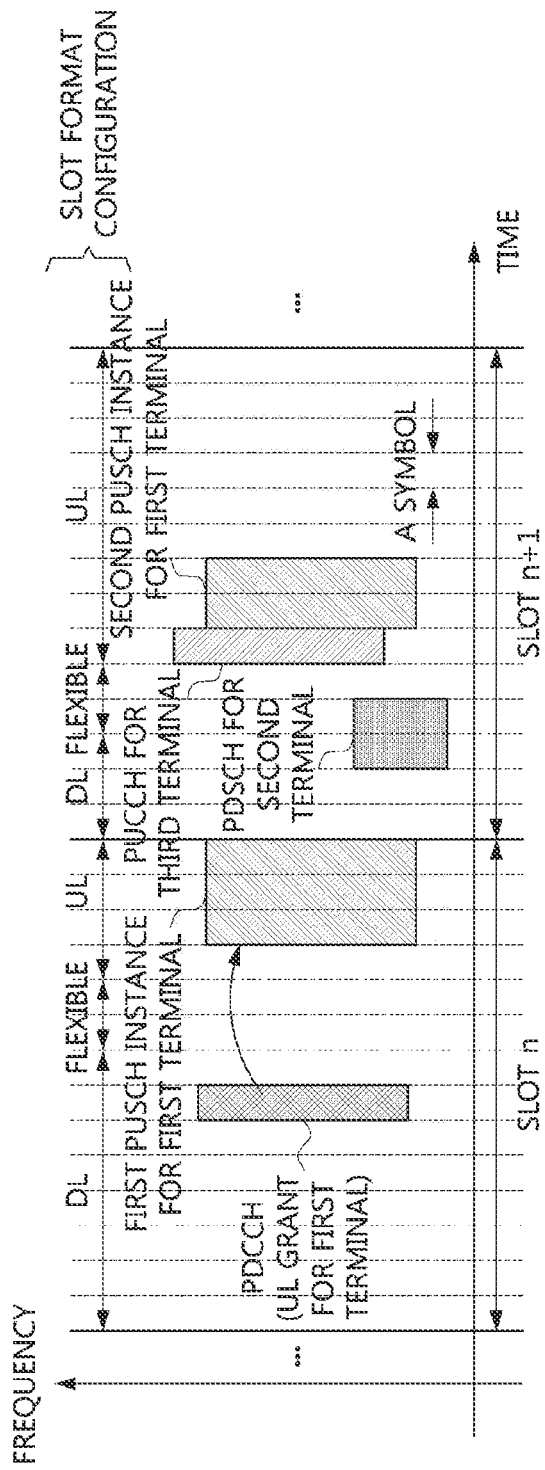
FIG. 6 is a timing diagram illustrating a sixth exemplary embodiment of a method for repetitive transmission of a PUSCH in a communication system.

FIG. 6 is a timing diagram illustrating a sixth exemplary embodiment of a method for repetitive transmission of a PUSCH in a communication system. For example, FIG. 6 may illustrate Method 120 and the detailed methods of Method 120.

Referring to FIG. 6, the base station may schedule PUSCH repetitive transmission for uplink URLLC transmission of the first terminal. In this case, it may be assumed that five symbols are needed to ensure transmission reliability of the PUSCH, and the first terminal may transmit the PUSCH after at least four symbols from a reception completion time of an uplink grant. In this case, the base station may determine that the twelfth to fourteenth symbols of the slot n are used for the first PUSCH instance for the first terminal. In addition, it may be assumed that a PDSCH (e.g., PDSCH by semi-static or semi-persistent scheduling) for the second terminal is transmitted in the third to fourth symbols of the slot n+1 and a PUCCH for the third terminal is transmitted in the sixth symbol of the slot n+1.

In this case, the earliest time when the second PUSCH instance for the first terminal can be transmitted without causing interference to the second terminal and the third terminal in the slot n+1 may be the seventh symbol. Accordingly, the base station may determine that the seventh to eighth symbols of the slot n+1 are used for the second PUSCH instance for the first terminal. In this case, according to Method 120, the base station may signal resource allocation information for the first and second PUSCH instances to the first terminal. According to Method 121, the resource allocation information may include information indicating a start symbol and a length of each of the PUSCH instances.

According to Method 122, the base station may inform the terminal of (S, L)=(11, 3) configured for the first PUSCH instance, and may inform the terminal of (S, L)=(6, 2) configured for the second PUSCH instance. In addition, the base station may inform the first terminal of a slot offset (e.g., 0) and/or a PUSCH mapping type (e.g., type B) for each of the PUSCH instances.

The start symbol and the length for the PUSCH instance in Method 121 may be defined differently from the start symbol and the length for the PUSCH instance in Method 122. For example, the start symbol of the first PUSCH instance may be a relative distance (e.g., symbol offset) with one symbol (e.g., a start symbol or end symbol) among symbol(s) occupied by a PDCCH including the uplink grant. In the exemplary embodiment shown in FIG. 6, the symbol offset may be 5.

In another example, the start symbol of the PUSCH instance(s) after the first PUSCH instance may be indicated as a relative distance with one symbol (e.g., a start symbol or end symbol) among symbol(s) constituting the previous PUSCH instance. In the exemplary embodiment shown in FIG. 6, the start symbol of the second PUSCH instance may be indicated by a symbol offset (e.g., 7) between the end symbol of the first PUSCH instance and the start symbol of the second PUSCH instance.

Meanwhile, a PUSCH instance preceding a certain PUSCH instance (e.g., a PUSCH instance immediately before the certain PUSCH instance) may be a PUSCH instance for the same TB or may be a PUSCH instance for another TB. For example, in the latter case, one uplink grant or one configured grant resource configuration may schedule a plurality of PUSCH instances for a plurality of TBs, and each TB may be transmitted through one or more PUSCH instances. In this case, the uplink grant or the configured grant resource configuration may include time domain resource allocation information (e.g., information about a start symbol, a length, a start slot, etc.) for the plurality of PUSCH instances. A certain TB among the plurality of TBs may be repeatedly transmitted through the plurality of PUSCH instances according to the methods according to the present disclosure. In this case, if PUSCH instance(s) preceding the plurality of PUSCH instances for the certain TB are allocated together, the start symbol of the first PUSCH instance of the certain TB may be indicated by a relative distance with one symbol among symbol(s) constituting a PUSCH instance for another previous TB (e.g., a TB immediately before the certain TB).

Meanwhile, in the following exemplary embodiments, some of the PUSCH instance(s) constituting the PUSCH repetitive transmission may be dropped. In this case, the start symbol of the PUSCH instance(s) after the first PUSCH instance may be indicated as a relative instance with one symbol (e.g., a start symbol or end symbol) among symbol(s) constituting the previous PUSCH instance that has not been dropped (e.g., the PUSCH instance that has been actually transmitted by the terminal).

The terminal may determine which slot each PUSCH instance is allocated to by determining the position of the start symbol of each PUSCH instance through the above-described methods. Therefore, in the proposed methods, the base station may not separately inform the terminal about which slot each PUSCH instance is mapped to. When it is determined that a PUSCH instance is allocated to a plurality of slots through the above-described methods, the terminal may regard resource allocation of the corresponding PUSCH instance as an error and may not transmit the corresponding PUSCH instance. Also, the terminal may not transmit PUSCH instance(s) after the corresponding PUSCH instance. It may not be expected in the terminal that such the case (e.g., the error in resource allocation of the PUSCH instance) occurs.

For another example, the start symbol of each PUSCH instance may be indicated by a relative distance from a reference time point (e.g., the first symbol of flexible symbol(s) and uplink symbol(s)) according to the slot format of the corresponding slot. In this case, the base station may signal to the terminal information on which slot each of PUSCH instance (e.g., PUSCH instances except the first PUSCH instance) is mapped to. The methods described above may be used in combination with Method 122. The above-described methods may be applied to some PUSCH instances, and Method 122 may be applied to the remaining PUSCH instances. For example, one of the methods described above may be applied to the first PUSCH instance, and Method 122 may be applied to subsequent PUSCH instance(s).

The above-described methods may be applied to communications according to the dynamic grant-based scheduling. For example, when a PUSCH is scheduled by a DCI with a CRC scrambled by C-RNTI or MCS-C-RNTI, the above-described methods may be applied. In addition, the above-described methods may be applied to communications according to the configured grant or semi-persistent scheduling (e.g., transmission of PUSCH and PDSCH).

Methods for determining the position of the start symbol of each PUSCH instance in communications according to the configured grant and semi-persistent scheduling may be identical or different. In addition, the methods described above may also be applied to a case in which a configured grant based PUSCH or a semi-persistently scheduled PDSCH is dynamically scheduled by a DCI (e.g., a DCI for activating or reactivating configured grant resources) with a CRC scrambled by CS-RNTI. In this case, even when communications according to the configured grant are performed, the scheduling scheme may be the same as the scheduling scheme according to the dynamic grant.

Meanwhile, in Method 120 to Method 122, a plurality of PUSCH instances may be mapped to one slot. In this case, the PUSCH may be repeatedly transmitted on a minislot basis or a subslot basis. This may be referred to as 'Method 123'. Here, the number of PUSCH instances may be different from the number of slots aggregated for PUSCH transmission. Accordingly, the base station may transmit to the terminal each of information indicating the number of PUSCH instances and information indicating the number of slots aggregated for PUSCH transmission. For example, an RRC parameter (e.g., aggregationFactorUL) or a DCI indicating the number of slots aggregated for PUSCH transmission may be transmitted to the terminal. In addition, the information indicating the number of PUSCH instances may be signaled to the terminal in an explicit or implicit manner. For example, when the number of PUSCH instances is signaled in an implicit manner, the terminal may consider that the number of PUSCH instances is equal to the number of (S, L) or SLIVs.

Method 123 may be applied when the number of slots aggregated for PUSCH transmission is one. For example, the terminal may identify that the number of slots aggregated for PUSCH transmission (e.g., aggregationFactorUL) is 1 through signaling of the base station and that the number of PUSCH instances is 2 or more. In this case, the terminal may assume that all PUSCH instances are scheduled in one slot (e.g., a PUSCH start slot indicated by a slot offset).

On the other hand, when it is identified that the number of slots aggregated for PUSCH transmission (e.g., aggregationFactorUL) is equal to the number of PUSCH instances, the terminal may assume that each PUSCH instance is scheduled in each slot. Method 123 may also be applied when a plurality of slots are aggregated for PUSCH transmission. In this case, mapping information between the PUSCH instance(s) and the slot(s) may be further signaled to the terminal. In more detail, the base station may transmit to the terminal information on which slot each PUSCH instance is mapped to. The number of PUSCH instances per slot may be the same in all aggregated slots. Alternatively, the number of PUSCH instances per slot may be different for each slot.

Figure 7:
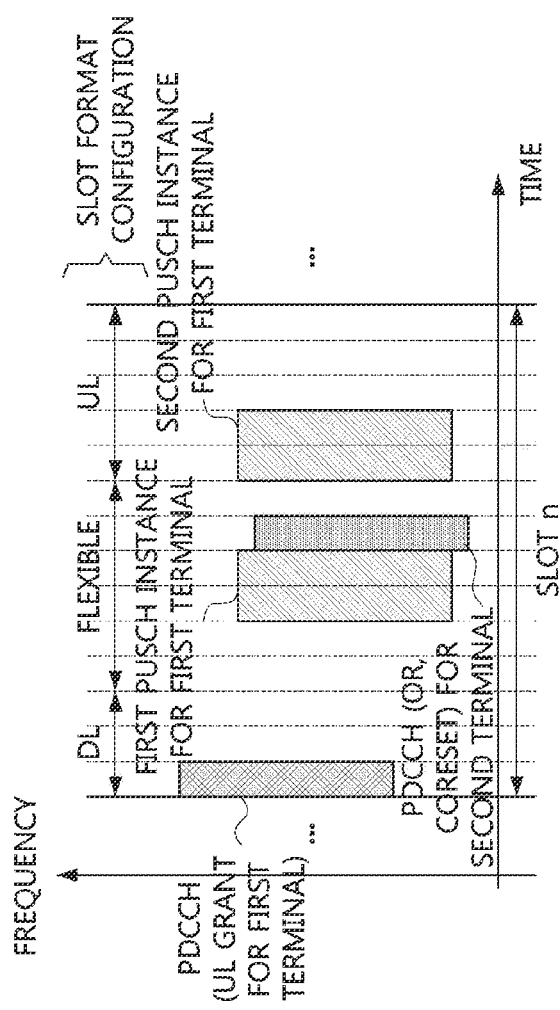
FIG. 7 is a timing diagram illustrating a seventh exemplary embodiment of a method for repetitive transmission of a PUSCH in a communication system.

FIG. 7 is a timing diagram illustrating a seventh exemplary embodiment of a method for repetitive transmission of a PUSCH in a communication system. For example, FIG. 7 illustrates an exemplary embodiment of PUSCH repetitive transmission in one slot according to Method 123.

Referring to FIG. 7, the base station may schedule PUSCH repetitive transmission for uplink URLLC transmission of the first terminal. In this case, it may be assumed that four symbols are needed to ensure transmission reliability of the PUSCH, and the first terminal may transmit the PUSCH after at least four symbols from a reception completion time of an uplink grant. In this case, a PUSCH resource for minimizing the transmission latency of the PUSCH and ensuring that the second terminal receives a PDCCH in the eighth symbol of the slot n may be allocated as shown in FIG. 7. For example, the base station may determine that the sixth to seventh symbols of the slot n are used for the first PUSCH instance for the first terminal, and the tenth to eleventh symbols of the slot n are used for the second PUSCH for the first terminal.

When a timing alignment value of the uplink timing of the first terminal is shorter than one symbol length, the ninth symbol of the slot n may serve as a guard interval. In this case, the time domain resource allocation information of each PUSCH instance may be signaled to the terminal by the above-described methods (e.g., Method 121, Method 122, etc.). For example, in Method 122, the base station may inform the first terminal of (S, L)=(5, 2) configured for the first PUSCH instance, and may inform the first terminal of (S, L)=(9, 2) configured for the second PUSCH instance. In addition, the base station may inform the first terminal of a slot offset (e.g., 0) and/or a PUSCH mapping type (e.g., type B) for each of the PUSCH instances. Here, the slot offset may be a slot offset between the PDCCH including the uplink grant and the first PUSCH instance.

Information on the start symbol and the length of the PUSCH instance may be transmitted to the terminal using at least one of DCI, RRC signaling, and a MAC CE. In Method 122, (S, L) or SLIV of each PUSCH instance may be informed to the terminal. For this, a time domain resource assignment field of a DCI (e.g., uplink grant) may be defined for each PUSCH instance or for each slot aggregated for PUSCH transmission.

Alternatively, time domain resource allocation candidate(s) configured by RRC signaling may include information on a plurality of PUSCH instances or a plurality of slots aggregated for PUSCH transmission. For example, a specific time domain resource allocation candidate may include (S, L) or SLIV(s) for two PUSCH instances. In this case, slot offset and PUSCH mapping type information may be common to the plurality of PUSCH instances or the plurality of slots aggregated for PUSCH transmission. The time domain resource allocation candidate(s) may be pre-configured to the terminal by RRC signaling, and one of the time domain resource allocation candidate(s) may be indicated by the time domain resource assignment field of the DCI (e.g., uplink grant). The terminal may use the time domain resource allocation candidate indicated by the time domain resource assignment field of the DCI among the time domain resource allocation candidate(s) configured by RRC signaling.

For example, the first time domain resource allocation candidate configured by RRC signaling may include a first SLIV and a second SLIV (or, first (S, L) and second (S, L)). In addition, the first time domain resource allocation candidate may further include a slot offset, a PUSCH mapping type, and/or an aggregation factor. The aggregation factor may mean the number of slots aggregated for PUSCH transmission. When a plurality of time domain resource allocation information is signaled to the terminal, the aggregation factor may be limited to the number of time domain resource allocation information (e.g., SLIVs) or less. In this case, the number of SLIVs may mean the number of PUSCH instances, the first SLIV may correspond to the first PUSCH instance, and the second SLIV may correspond to the second PUSCH instance.

For example, when the aggregation factor is 1, two PUSCH instances may be scheduled in one slot. When the aggregation factor is 2, two PUSCH instances may be scheduled in each of the two slots. The aggregation factor may be set to be larger than the number of time domain resource allocation information (e.g., SLIVs). In this case, the aggregation factor may mean the number of PUSCH instances, and one PUSCH instance may be scheduled in each of the slots aggregated for PUSCH transmission. For example, when the aggregation factor is 3, the first SLIV and the second SLIV may correspond to three PUSCH instances. One SLIV may correspond to a plurality of PUSCH instances.

For another example, the second time domain resource allocation candidate configured by RRC signaling may include the first SLIV. In addition, the second time domain resource allocation candidate may further include a slot offset, a PUSCH mapping type, and/or an aggregation factor. When there is one SLIV, the aggregation factor may mean the number of slots aggregated for PUSCH transmission, and one PUSCH instance may be scheduled in each slot. The first SLIV may correspond to all PUSCH instances. The first and second time domain resource allocation candidates may constitute the same RRC table. For example, the first and second time domain resource allocation candidates may be included in PUSCH configuration information for the same carrier and the same BWP, and the PUSCH configuration information may be transmitted to the terminal through RRC signaling. The base station may transmit a DCI indicating one time domain resource allocation candidate among the first and second time domain resource allocation candidates configured by RRC signaling to the terminal. Here, the number of SLIVs may be dynamically changed by scheduling of the base station. Table 3 below may be an RRC table indicating time domain resource allocation candidate(s) configured by RRC signaling.

TABLE 3

| Time domain resource allocation candidate index | PUSCH mapping type | Slot offset | First SLIV | Second SLIV | Aggregation factor |
|---|---|---|---|---|---|
| 0 | Type B | 0 | A1 | — | 1 |
| 1 | Type B | 0 | B1 | B2 | 2 |
| 2 | Type B | 0 | C1 | C2 | 1 |

The RRC table of Table 3 may include three time domain resource allocation candidates. The time domain resource allocation candidate having an index of 0 may include one SLIV. This may correspond to the existing time domain resource allocation scheme. The time domain resource allocation candidate having the index of 0 may correspond to the above-mentioned second time domain resource allocation candidate. The time domain resource allocation candidate having an index of 1 may include two SLIVs, the first SLIV may be set to B1, and the second SLIV may be set to B2. The time domain resource allocation candidate having an index of 2 may include two SLIVs, the first SLIV may be set to C1, and the second SLIV may be set to C2.

According to Method 120 to Method 123, when a time domain resource assignment field of the DCI (e.g., uplink grant) received at the terminal indicates the index 1 or 2 of Table 3, the terminal may consider that a PUSCH scheduled by the DCI consists of two PUSCH instances. In this case, the terminal may determine the symbol position of the first PUSCH instance using the first SLIV, and may determine the symbol position of the second PUSCH instance using the second SLIV. When the aggregation factor is 2 (e.g., when the DCI indicates the index 2), the terminal may consider that the first PUSCH instance is allocated to the first slot, and the second PUSCH instance is allocated to the second slot. When the aggregation factor is 1 (e.g., when the DCI indicates the index 1), the terminal may consider that the first and second PUSCH instances are allocated to the same slot.

The RRC table configuration of Table 3 is only one exemplary embodiment of the above-described method, and the parameter set constituting the RRC table may be configured in various forms by the above-described method. For example, when a PUSCH mapping type is indicated for each PUSCH instance or each TB (e.g., for each set of PUSCH instances constituting a TB), an entry (e.g., each time domain resource allocation candidate) of the RRC table may include a plurality of PUSCH mapping type information. For another example, when a slot offset is indicated for each PUSCH instance or each TB (e.g., for each set of PUSCH instances constituting a TB), an entry of the RRC table may include a plurality of slot offset information. As another example, some entries in the RRC table may not include the aggregation factor. Alternatively, a method of interpreting the aggregation factor for each entry of the RRC table may be different. For example, the terminal may regard the aggregation factor as the number of PUSCH instances for some entries, and regard the aggregation factor as the number of slots to which the PUSCH instance(s) are mapped for some other entries.

When the dynamic grant based scheduling scheme is used in the above-described methods (e.g., when the PUSCH is scheduled by a DCI with a CRC scrambled by C-RNTI or MCS-C-RNTI), time domain resource allocation information of PUSCH instances may be signaled to the terminal through one PDCCH (e.g., one DCI format). This method may also be applied when the type 2 configured grant-based scheduling scheme (e.g., when the PUSCH is scheduled by a DCI (e.g., DCI activating or reactivating the configured grant resources) with a CRC scrambled by CS-RNTI) is used. When a PDSCH is repeatedly transmitted, the type 2 configured grant-based scheduling scheme may correspond to the downlink semi-static or semi-persistent scheduling scheme.

On the other hand, in the case of PUSCH and PDSCH transmission according to the configured grant (or semi-persistent scheduling), the base station may schedule a PUSCH or a PDSCH to the terminal through RRC signaling and/or DCI. The scheduling may continue semi-persistently until reconfigured by the base station. In particular, a resource region (hereinafter, referred to as a 'configured grant resource') in which the PUSCH or the PDSCH can be transmitted may appear periodically and repeatedly, and information indicating a periodicity of the configured grant resource and the position of the configured grant resource (e.g., a slot or symbol offset between the start of period and the position of the configured grant resource) according to the periodicity may be signaled from the base station to the terminal. The start point of the period of the configured grant resource may be derived from a predefined reference point. For example, scheduling information for a type 1 configured grant PUSCH may be configured to the terminal through RRC signaling. Scheduling information for a type 2 configured grant PUSCH and a semi-persistently scheduled PDSCH may be configured (e.g., indicated) to the terminal through a combination of RRC signaling and DCI.

The terminal may determine whether to transmit the PUSCH in the configured grant resource according to the presence, shape, size, and the like of uplink traffic. On the other hand, the terminal may expect that the PDSCH is always transmitted in the configured grant resource. Alternatively, the terminal may expect that the PDSCH is opportunistically transmitted in the configured grant resource. Initial transmission of the configured grant-based PUSCH and PDSCH may be performed in the configured grant resource. Retransmission of the configured grant-based PUSCH and PDSCH may be performed on resources that are dynamically scheduled by DCI. Re-scheduling (or, reactivation, re-initialization, or the like) of the configured grant-based PUSCH or PDSCH and retransmission of the configured grant-based PUSCH or PDSCH according to the re-scheduling may be performed in a resource dynamically scheduled by DCI. In these cases, a CRC of the DCI may be scrambled by CS-RNTI.

In the configured grant-based transmission, the PUSCH or PDSCH may be repeatedly transmitted. For example, the configured grant-based PUSCH or PDSCH may be repeatedly transmitted within one period. To this end, one or a plurality of configured grant resource(s) may be configured to the terminal within one period. For example, the configured grant resource(s) may be mapped within a predetermined time period (e.g., duration), and the configured grant resource(s) may be arranged periodically and repeatedly. One PUSCH or PDSCH instance may be transmitted in one configured grant resource. The plurality of PUSCH or PDSCH instances may be transmitted in a plurality of configured grant resources (e.g., logically consecutive configured grant resources). In this case, the above-described method may be used for configuring and indicating the configured grant resource.

Figure 8:
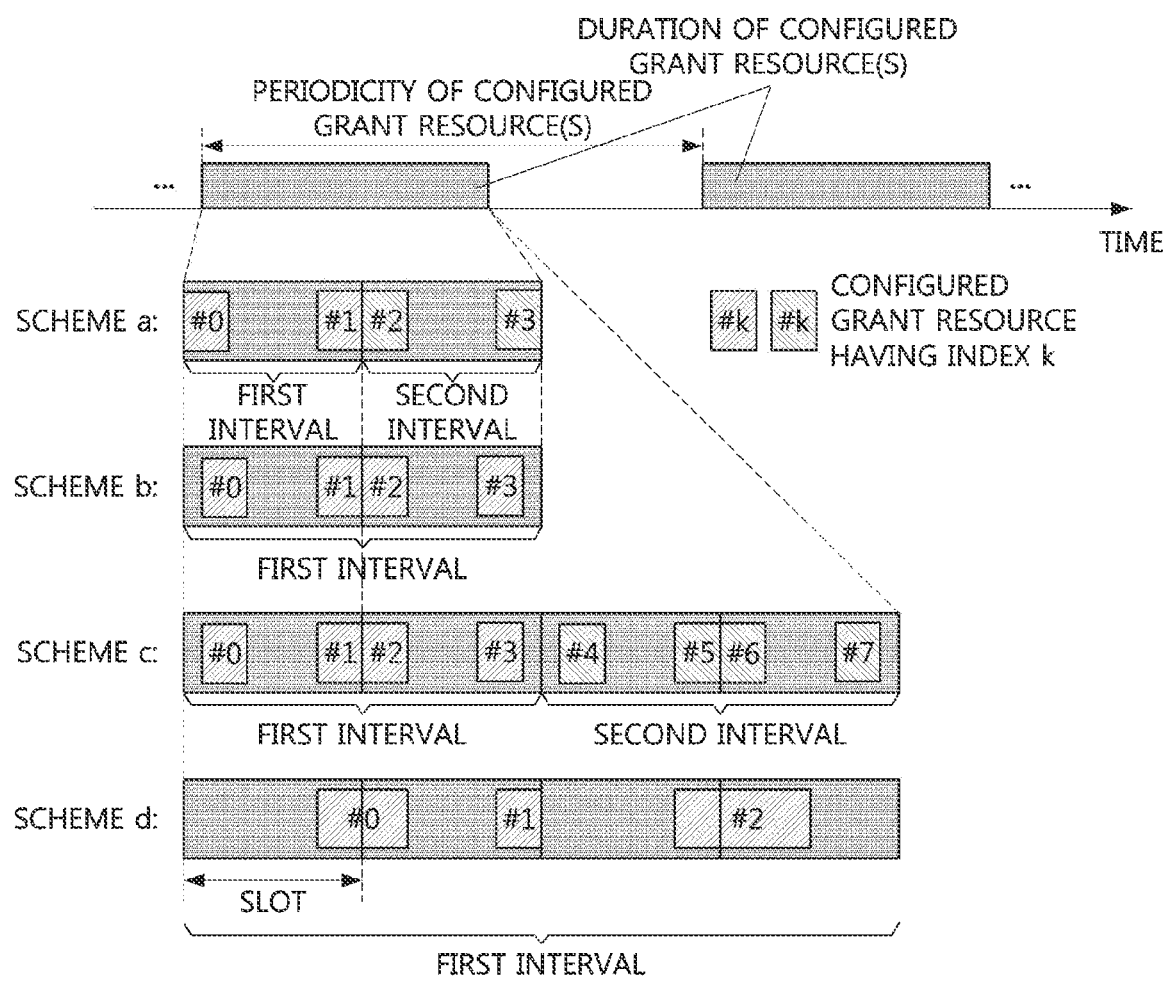
FIG. 8 is a timing diagram illustrating a first exemplary embodiment of a method for configuring configured grant resources for repetitive transmission in a communication system.

FIG. 8 is a timing diagram illustrating a first exemplary embodiment of a method for configuring configured grant resources for repetitive transmission in a communication system.

Referring to schemes a and b shown in FIG. 8, four configured grant resources may be mapped to a predetermined time interval (e.g., two consecutive slots). The four configured grant resources may be repeated periodically. Referring to a scheme c shown in FIG. 8, eight configured grant resources may be mapped to a predetermined time interval (e.g., four consecutive slots). Eight configured grant resources may be repeated periodically. Referring to a scheme d shown in FIG. 8, three configured grant resources may be mapped to a predetermined time interval (e.g., four consecutive slots). Three configured grant resources may be repeated periodically. Within one period, the configured grant resource(s) may be repeatedly arranged in units of a slot or in units of a time unit shorter than one slot.

Method 120 to Method 123 may be used for repetitive transmission of configured grant-based PUSCH and PDSCH. For example, in order to configure periodic configured grant resources, A time domain resource allocation information (e.g., at least one information of A SLIVs or A (S, L), A slot offsets, and A PUSCH mapping types) may be configured (e.g., indicated) to the terminal. Here, A may be a natural number. Each time domain resource allocation information (e.g., each SLIV or each (S, L)) may be used to determine the time domain position of at least one configured grant resource within one period. As described above, in order to determine the configured grant resource in the time domain, a periodicity of the configured grant resource and an offset of the configured grant resource (or a predetermined time interval) within the corresponding period may be used together. The above-described exemplary embodiments may be performed by various methods. The exemplary embodiments below may be performed based on Method 121.

In the scheme a, two SLIVs may be signaled to the terminal for configuration of the configured grant resources. That is, A may be two. Within one period, the terminal may determine a start symbol and a duration of each of the configured grant resources #0 and #1 of the first slot using the two SLIVs. In this case, the configured grant resources #0 and #1 may be disposed in the same slot. Two SLIVs may be equally applied in two consecutive slots. Accordingly, the terminal may determine a start symbol and a duration of each of the configured grant resources #2 and #3 of the second slot using two SLIVs.

The position of symbols for the configured grant resource #0 in the slot may be the same as the position of symbols for the configured grant resource #2 in the slot, and the position of symbols for the configured grant resource #1 in the slot may be the same as the position of symbols for the configured grant resource #3 in the slot. That is, the A configured grant resource(s) may be mapped to the same slot by the A time domain resource allocation information, and the A configured grant resource(s) may be repeatedly arranged in the B consecutive slots. Within one period, A×B configured grant resource(s) may be allocated to B slots. Here, B may be a natural number.

In the scheme b and scheme c, four SLIVs may be signaled to the terminal for configuration of the configured grant resources. That is, A may be four. The terminal may determine a start symbol and a duration of each of the configured grant resources #0 to #3 in two slots of a first interval using four SLIVs. In the scheme b, the number of periods to which the SLIVs are repeatedly applied within one period may be 1. That is, B may be 1. In the scheme c, the number of intervals to which the SLIVs are repeatedly applied within one period may be 2. That is, B may be 2. Accordingly, the terminal may determine a start symbol and a duration of each of the configured grant resources #4 to #7 in two slots of a second interval using four SLIVs.

The position of the slot to which each configured grant resource is mapped may be configured to the terminal through separate signaling. For example, the position of the slot of the first configured grant PUSCH resource may be represented by information about the slot offset from the start point of the period (e.g., the first slot of the period), and the position information (e.g., the slot offset) of the first configured grant resource may be transmitted to the terminal. Alternatively, the slot to which each configured grant resource is mapped or some configured grant resources are mapped may be determined by the SLIVs. For example, the terminal may regard S (e.g., the start symbol of the configured grant resource) corresponding to the SLIV as a symbol offset with one symbol (e.g., the first symbol) constituting the previous configured grant resource. In exceptional cases, S corresponding to the SLIV for the first configured grant resource may mean a distance from the start point of the first slot (e.g., offset with the first symbol of the first slot). The terminal may obtain information indicating the offset of the configured grant resource from the base station through signaling, and may determine the position of the first slot to which the configured grant resource is mapped using the offset.

In the scheme d, three SLIVs may be signaled to the terminal for configuration of the configured grant resources. That is, A may be three. The terminal may determine a start symbol and a duration of each of the configured grant resources #0 to #2 in four slots using three SLIVs. In this case, the number of intervals to which the SLIVs are repeatedly applied may be 1. That is, B may be 1. The specific configured grant resource may be mapped to a plurality of slots. For example, the configured grant resource #0 may be mapped to the first and second slots, and the configured grant resource #2 may be mapped to the third and fourth slots. This mapping operation may be performed by configuring the SLIVs or (S, L) such that a sum of S and L for each of the configured grant resources #0 and #2 is greater than 14.

In the scheme d, (at most) one configured grant resource may be limited to be started in one slot. That is, each configured grant resource may be started in a different slot. Each of the configured grant resources #0, #1, and #2 may be mapped to start from the first, second, and third slots, respectively. The terminal may assume that S corresponding to each of the first, second, and third SLIVs is disposed in each of the first, second, and third slots. In addition, the terminal may assume that S corresponding to each of the first, second, and third SLIVs is a symbol derived based on each of the first, second, and third slots.

That is, A configured grant resources may be mapped to C consecutive slots within one period. C may be a natural number. The position of symbols for each of the A configured grant resources may be determined through A SLIVs. The C slots may be repeated B times (continuously) in the time domain. In this case, A×B configured grant resources may be configured by one configured grant resource configuration, and the A×B configured grant resources may be disposed in B×C consecutive slots. Configuration information of the one configured grant resource may include A SLIVs (or A time domain resource allocation information), and may be configured (e.g., indicated) to the terminal through RRC signaling and/or DCI. The DCI may be a DCI for scheduling a PUSCH or PDSCH (e.g., DCI formats 0_0, 0_1, 1_0, 1_1, etc.), and one DCI may include all SLIV(s) corresponding to the configuration information of one configured grant resource. The base station may signal B (e.g., repetition pattern of SLIV(s)) within one period to the terminal explicitly or implicitly. For example, the terminal may obtain a parameter (e.g., aggregation factor) configured by the base station, and may interpret that the parameter (e.g., aggregation coefficient) is B. Alternatively, B may be explicitly configured to the terminal by a new parameter.

The above-described exemplary embodiments may correspond to a case in which the terminal is instructed or configured to repeatedly transmit a PUSCH for one TB through one scheduling. However, this is only a specific exemplary embodiment, and the methods according to the present disclosure may be used for PUSCH repetitive transmission of a specific TB when the terminal is instructed or configured to transmit PUSCH for a plurality of TBs through one scheduling.

In the above-described methods, frequency domain resource allocation information may be commonly applied to all data channel instances (e.g., PUSCH instances, PDSCH instances, or PSSCH instances) for the same TB. Other scheduling information (e.g., MCS, HARQ process ID, new data indicator (NDI), antenna port, number of transmission layers, power control information, etc.) may be common to all data channel instances for the same TB. In addition, configuration of QCL, transmission beam, precoding, and the like may be applied in common to all data channel instances for the same TB.

Meanwhile, as described above, a different RV may be applied to each data channel instance for the same TB. For example, a value of 0, 1, 2, or 3 may be used as the RV for each data channel instance. The RV of the first data channel instance may be informed by the base station to the terminal by DCI or RRC signaling. The RV(s) of the data channel instance(s) after the first data channel instance may be determined by a predefined pattern according to the RV of the first data channel instance. Alternatively, an RV for each data channel instance may be signaled to the terminal. Alternatively, the terminal may determine the RV for each data channel instance, and transmit each RV together with the corresponding data channel instance to the base station. For example, the uplink control information including the RV may be mapped to a part of the resource region of the PUSCH instance, and the corresponding uplink control information may be transmitted to the base station together with the PUSCH instance. In this case, separate channel coding may be applied to the uplink control information including the RV and the UL-SCH of the PUSCH instance. For example, a polar code may be applied to the former (i.e., uplink control information), and a low-density parity check (LDPC) code may be applied to the latter (i.e., PUSCH instance).

In case of the configured grant based PUSCH (or semi-persistently scheduled PDSCH), the pattern of RVs applied to the respective configured grant resources may be predefined in a standard specification. Alternatively, the base station may configure (e.g., indicate) a pattern of the RVs applied to the respective configured grant resources. For example, the RV pattern may be (0, 2, 3, 1). In this case, within one period, the RV may be sequentially applied from the first configured grant resource in the order of 0, 2, 3, 1, 0, 2, 3, 1, . . . , and the like. As another example, the RV pattern may be (0, 3, 0, 3) or (0, 0, 0, 0). The base station may start the PDSCH repetitive transmission in the configured grant resource to which RV=0 is applied, and the terminal may start the PUSCH repetitive transmission in the configured grant resource to which RV=0 is applied. For example, the terminal may transmit the first PUSCH instance in the configured grant resource to which RV=0 is applied, and may sequentially transmit the PUSCH instance(s) after the first PUSCH instance in the subsequent configured grant resource(s). When there are a plurality of configured grant resources to which RV=0 is applied within a period of one configured grant resource, the terminal may perform PUSCH repetitive transmission from one configured grant resource among the plurality of configured grant resources to which RV=0 is applied. Alternatively, the terminal may start the repeated PUSCH transmissions in the first configured grant resource to which RV=0 is applied.

In the configured grant-based repetitive transmission, the number of PUSCH instances actually transmitted within one period (or consecutive periods) may vary according to the start time of the PUSCH (or PDSCH) repetitive transmission. The terminal may repeatedly transmit the PUSCH until the last configured grant resource within the same period regardless of the start time of the repetitive PUSCH transmission. Alternatively, the number (e.g., maximum number) of PUSCH instances transmitted within one period may be configured to the terminal. For example, in a communication system supporting URLLC services, the maximum number of PUSCH instances that a terminal can transmit within one period may be set to 2 due to a limitation of latency.

The above-described methods may be applied when the PUSCH mapping type B is used. When the PUSCH mapping type is set (e.g., indicated) to B, the terminal may expect that the above-described resource allocation information is signaled from the base station. Information indicating the PUSCH mapping type may be transmitted to the terminal by DCI and/or RRC signaling for each PUSCH scheduling. Referring to Table 2, since the range of valid S and L values when the PUSCH mapping type A is used is limited, the PUSCH mapping type A may not be suitable for URLLC transmission. On the other hand, when the PUSCH repetitive transmission is for eMBB transmission, the above-described methods may be preferably applied to the PUSCH mapping types A and B.

The following exemplary embodiments may be signaling methods for distinguishing the above-described resource allocation method from the legacy resource allocation method. As a first exemplary embodiment of the implicit signaling method, the above-described resource allocation method may be applied when the PUSCH is scheduled by a specific DCI format. For example, in the NR communication system, a new DCI format having a smaller payload size than the existing DCI formats 0_0 and 1_0 may be introduced. The payload of the new DCI format may be set smaller than the payloads of the existing DCI formats 0_0 and 1_0. The terminal may assume that the above-described resource allocation method is applied when the PUSCH is scheduled by a new DCI format. When Method 122 is used, the terminal may consider that the time domain resource assignment field of the new DCI format is configured according to the above-described signaling method, and the terminal may obtain (S, L) or SLIV for each PUSCH instance from the corresponding time domain resource assignment field. Alternatively, the new DCI format may be replaced with the existing DCI format (e.g., DCI formats 0_1 and 1_1), and a method in which the terminal reinterprets all or some fields of the existing DCI format may be defined.

As a second exemplary embodiment of the implicit signaling method, the above-described resource allocation method may be applied when the PUSCH is scheduled by a DCI with a CRC scrambled by a specific RNTI. The specific RNTI may be C-RNTI or MCS-C-RNTI. Alternatively, the specific RNTI may be a new RNTI (e.g., second C-RNTI). Alternatively, the specific RNTI may be an RNTI configured by the base station to apply the above-described resource allocation method among a plurality of RNTIs (e.g., existing RNTIs and a new RNTI). For example, when Method 122 is used, the terminal may consider that a time domain resource assignment field of the DCI with the CRC scrambled by the specific RNTI is configured according to the above-described signaling method, and may obtain (S, L) or SLIV for each PUSCH instance from the corresponding time domain resource assignment field.

Meanwhile, whether to apply the above-described resource allocation method may be explicitly signaled to the terminal through a specific field of the DCI. Alternatively, whether to apply the above-described resource allocation method may be implicitly signaled to the terminal through the existing field of the DCI. For example, when Method 120 and the detailed methods of Method 120 are used, the terminal may distinguish the above-described resource allocation method from the existing resource allocation method through resource allocation information (e.g., the number of SLIVs) constituting the RRC table (e.g., the RRC table shown in Table 3). Alternatively, the information indicating whether to apply the above-described resource allocation method may be configured to the terminal through separate higher layer signaling (e.g., RRC signaling).

In the above resource allocation methods, each PUSCH instance may include a DM-RS. When the PUSCH mapping type B is applied, the DM-RS may be mapped to at least the first symbol of each PUSCH instance. In this case, when the DM-RS cannot be mapped from the first symbol of the PUSCH instance due to a certain condition, the DM-RS may be mapped from one symbol among the symbol(s) after the first symbol according to a predefined rule. For example, when some PRBs of the first symbol of the PDSCH instance overlap with a CORESET in downlink communication, the DM-RS for demodulation of the PDSCH may be mapped from the second symbol or to the second symbol. Meanwhile, the plurality of PUSCH instances may share the DM-RS. When a plurality of PUSCH instances are mapped to one slot, the first PUSCH instance of the corresponding slot may include the DM-RS, and the DM-RS included in the first PUSCH instance may be shared with the remaining PUSCH instance(s). That is, the base station may demodulate all the PUSCH instances in the slot using the DM-RS of the first PUSCH instance in the same slot. In this case, the same QCL, transmission beam, precoding, etc. may be applied to the PUSCH instances sharing the DM-RS.

In the above-described methods, the maximum value of the number of slots or the number of PUSCH instances aggregated for PUSCH transmission may be configured to the terminal. This method may be applied when a method in which the base station does not signal the number of slots or PUSCH instances actually aggregated for PUSCH transmission to the terminal is used (e.g., when Method 110 is used). For example, when the maximum value of the number of slots aggregated for PUSCH transmission is M, the terminal may transmit the PUSCH instances in consecutive M slots from the PUSCH start slot. When some PUSCH instances are mapped to slots after the consecutive M slots, the terminal may not transmit the corresponding PUSCH instance. Here, M may be a natural number. When one uplink grant or one configured grant resource configuration includes PUSCH resource allocation information for a plurality of TBs, the maximum value may be the maximum number of slots for each TB or the maximum number of PUSCH instances for each TB. Alternatively, the maximum value may be the maximum number of slots for all TBs or the maximum number of PUSCH instances for all TBs.

[TBS Determination Method]

In the NR communication system, a transport block size (TBS) for a data channel (e.g., PUSCH, PDSCH, or PSSCH) may be determined according to a function of the total number of REs or an approximation of the total number of REs allocated to the data channel (hereinafter referred to as '$N_{RE}$'). The terminal may calculate $N_{RE}'$ ($=N_{sc}^{RB} \times N_{symb}^{sh} - N_{DMRS}^{PRB} - N_{oh}^{PRB}$). Here, $N_{sc}^{RB}$ may be the number of subcarriers per RB, $N_{symb}^{sh}$ may be the number of symbols allocated to the data channel within a slot, $N_{DMRS}^{PRB}$ may be the number of REs for DM-RS per PRB considering the overhead of a DM-RS code division multiplexing (CDM) group without data, and $N_{oh}^{PRB}$ may be an overhead value configured by the base station. The terminal may derive the $N_{RE}$ from the calculated $N_{RE}'$. For example, the terminal may derive $N_{RE}$ according to $N_{RE}=\min(156, N_{RE}')\times n_{PRB}$. Here, $n_{PRB}$ may be the number of PRBs allocated to the terminal for the data channel.

Then, the terminal may derive a median value $N_{info}$ of information bits from $N_{RE}$. For example, the terminal may derive $N_{info}$ according to $N_{info}=N_{RE}\times R\times Q_m\times v$. Here, R may be a target code rate, $Q_m$ may be a modulation level, and v may be the number of transmission layers. R, $Q_m$, and v may be dynamically scheduled to the terminal through DCI. Alternatively, R, $Q_m$, and v may be semi-persistently scheduled to the terminal through RRC signaling.

Then, when $N_{info}$ is less than or equal to a reference value, the terminal may convert $N_{info}$ to a quantized value according to a predefined equation, and select a TBS having a value closest to the converted value in a predefined table. On the other hand, when $N_{info}$ exceeds the reference value, the terminal may directly derive a TBS using $N_{info}$ and a predefined equation. The above-described procedure may be applied when $I_{MCS}$ is assigned with an entry having both R and $Q_m$ (e.g., $0 \leq I_{MCS} \leq 27$ or $0 \leq I_{MCS} \leq 28$). When $I_{MCS}$ is not assigned with an entry having both R and $Q_m$, the terminal may assume the same TBS as the previous transmission of the same TB. When data is repeatedly transmitted, $N_{RE}'$ may be the total number of REs allocated to each data channel instance or an approximation of the total number of REs.

When the above-described resource allocation methods are used, the durations of PUSCH instances may be different. In addition, DM-RS overhead may be different for each PUSCH instance. That is, the number of REs or $N_{RE}'$ of data may be different for each PUSCH instance. In this case, if the above-described TBS determination method is applied for each PUSCH instance, a different TBS may be derived for each PUSCH instance. Therefore, there is a need for a method of determining a common TBS for all PUSCH instances constituting PUSCH repetitive transmission.

As a first exemplary embodiment of determining the common TBS, the TBS may be determined based on the sum of the REs allocated to all PUSCH instances or an approximation of the sum of REs. For example, when the TBS determination method is equally applied, the terminal may regard $N_{symb}^{sh}$ as the sum of the number of symbols occupied by all PUSCH instances. In addition, the terminal may regard $N_{DMRS}^{PRB}$ as the sum of the number of REs of DM-RS per PRB for all PUSCH instances. Accordingly, $N_{RE}'$ may be defined as in Equation 2 below.

$$N_{RE}'=N_{sc}^{RB}\times(N^{sh}_{symb,0}+\ldots+N^{sh}_{symb,V-1})-(N^{PRB}_{DMRS,0}+\ldots+N^{PRB}_{DMRS,V-1})-N^{PRB}_{oh} \quad \text{[Equation 2]}$$

In Equation 2, $N_{symb,i}^{sh}$ and $N_{DMRS,i}^{PRB}$ may be the number of symbols for the (i+1)-th PUSCH instance and the number of REs of the DM-RS, respectively. V may be the number of PUSCH instances. Here, it may be defined as 'i=0, . . . , V−1'. In Method 110, since a plurality of PUSCH instances are considered as one PUSCH from a base station perspective, the TBS may be determined based on the total number of REs. This method may be applied to other resource allocation methods (e.g., Method 120 to Method 123).

Meanwhile, TBS may be determined based on an average of the number of REs allocated to each PUSCH instance or an approximation corresponding to the average of the number of REs. The average of the number of REs may mean an average for all PUSCH instances. For example, when the TBS determination method is applied in the same manner, the terminal may regard $N_{symb}^{sh}$ as an average of the number of symbols occupied by each PUSCH instance. In addition, the terminal may regard $N_{DMRS}^{PRB}$ as an average of the number of REs of DM-RS per PRB for each PUSCH instance. Accordingly, $N_{RE}'$ may be defined as in Equation 3 below.

$$N_{RE}'=N_{sc}^{RB}\times 1/V\times(N^{sh}_{symb,0}+\ldots+N^{sh}_{symb,V-1})-1/V\times(N^{PRB}_{DMRS,0}+\ldots+N^{PRB}_{DMRS,V-1})-N^{PRB}_{oh} \quad \text{[Equation 3]}$$

The above-described TBS determination method may be appropriate when Method 120 to Method 123 or a conventional slot-based PUSCH repetitive transmission method is used for PUSCH resource allocation. Also, the above-described TBS determination method may be applied to other resource allocation methods (e.g., Method 110). Equation 4 may be used when a plurality of PUSCH instances are transmitted in some slots. Equation 4 may be a modified equation based on Equation 3. The average number of REs may mean an average of slots aggregated for PUSCH transmission. In Equation 4, W may mean the number of slots that are aggregated.

$$N_{RE}'=N_{sc}^{RB}\times 1/W\times(N^{sh}_{symb,0}+\ldots+N^{sh}_{symb,V-1})-1/W\times(N^{PRB}_{DMRS,0}+\ldots+N^{PRB}_{DMRS,V-1})-N^{PRB}_{oh} \quad \text{[Equation 4]}$$

[PUSCH Instance Dropping]

In the above resource allocation methods, the slots aggregated for PUSCH transmission may be slots which are contiguous in time. However, some slots may not be suitable for PUSCH transmission. "When a slot satisfies a specific condition" or "When a resource allocated for PUSCH instance transmission in a certain slot satisfies a specific condition", the terminal may omit transmission of PUSCH instance in the corresponding slot. For example, when the number of symbols in which the PUSCH can be transmitted in some of the slots aggregated for PUSCH transmission is equal to or less than a reference value (hereinafter, referred to as '$N_{th}$'), the terminal may omit transmission of the PUSCH instance in the corresponding slot. $N_{th}$ may be a natural number. $N_{th}$ may be predefined in the specification. Alternatively, the base station may configure $N_{th}$, and may inform the terminal of the configured $N_{th}$. Alternatively, when a PUSCH instance satisfies a specific condition regardless of slot configuration, transmission of the corresponding PUSCH instance may be dropped. This may be referred to as 'Method 200'.

For example, symbols in which the PUSCH can be transmitted in a slot may include flexible symbol(s) and uplink symbol(s), and a transmission direction of the symbols may be determined according to a semi-static slot format configuration or a dynamic slot format indication. In the case of configured grant PUSCH, symbols in which the PUSCH can be transmitted may include flexible symbol(s) and uplink symbol(s) by semi-static configuration. Also, the symbols in which the PUSCH can be transmitted may include uplink symbol(s) by dynamic indication. Alternatively, the symbols in which the PUSCH can be transmitted may be the above-described set of valid symbols. The terminal may drop a certain PUSCH instance when the duration of the corresponding PUSCH instance scheduled by the above-described methods is not included in the above-described set of valid symbols.

Figure 9A:
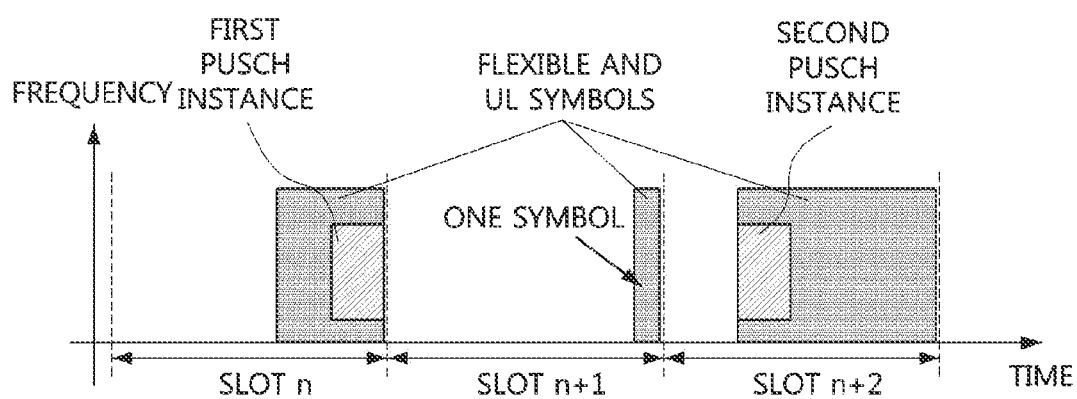
FIG. 9A is a timing diagram illustrating an eighth exemplary embodiment of a method for repetitive transmission of a PUSCH in a communication system.
Figure 9B:
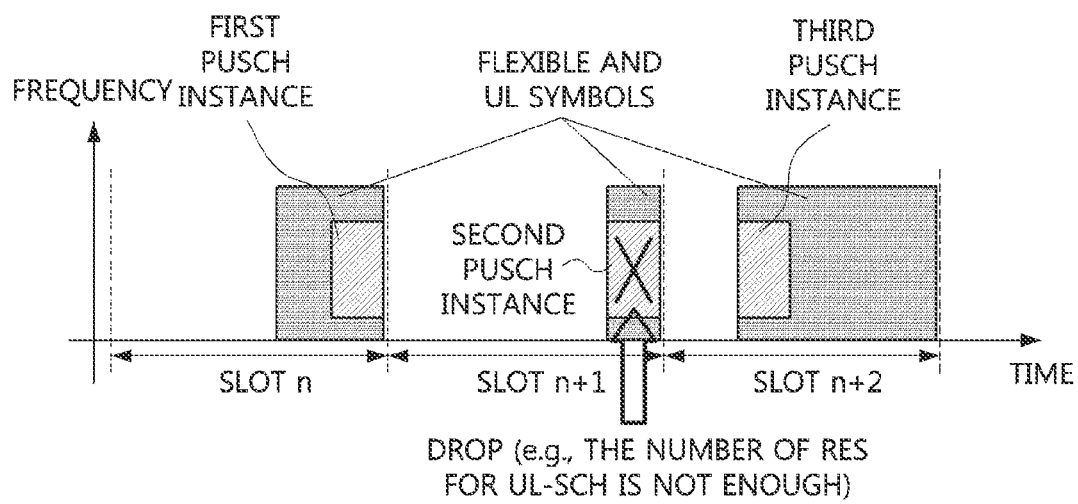
FIG. 9B is a timing diagram illustrating a ninth exemplary embodiment of a method for repetitive transmission of a PUSCH in a communication system.

FIG. 9a is a timing diagram illustrating an eighth exemplary embodiment of a method for repetitive transmission of a PUSCH in a communication system, and FIG. 9b is a timing diagram illustrating a ninth exemplary embodiment of a method for repetitive transmission of a PUSCH in a communication system. For example, FIG. 9A may be an exemplary embodiment of PUSCH repetitive transmission in one slot according to Method 200 and FIG. 9A may be an exemplary embodiment of PUSCH repetitive transmission in one slot according to Method 210.

Referring to FIG. 9A, a PUSCH may be repeatedly transmitted from the slot n. In the slot n+1, the sum of the number of flexible symbol(s) and the number of uplink symbol(s) may be 1. When Nth is 1, the terminal may not transmit a PUSCH instance in the slot n+1 according to the Method 130. The above-described resource allocation methods (e.g., Method 110 and Method 120) may be used in combination with Method 200. For example, when the PUSCH is scheduled to the terminal by Method 110 (e.g., when the duration of some PUSCH instances is determined implicitly), the terminal may determine whether to transmit the PUSCH in the slot(s) after the PUSCH start slot through Method 200.

For another example, when the PUSCH is scheduled to the terminal by Method 120 or the detailed methods of Method 120, the terminal may determine the positions of the slot(s) aggregated for PUSCH transmission in consideration of Method 200. That is, when some slots satisfy a certain condition and are not used for PUSCH transmission, the slots aggregated for PUSCH transmission may not be contiguous in time.

The slots aggregated in the exemplary embodiment shown in FIG. 9A may include the slot n and the slot n+2. In this case, the base station may signal to the terminal each of information indicating the aggregation factor indicating the number of aggregated slots including the dropped slots and information indicating the number of transmitted PUSCH instances including the dropped PUSCH instances. That is, each of the nominal aggregation factor and the number of transmitted PUSCH instances may be three. The transmitted PUSCH instance may mean a PUSCH instance transmitted from the base station to the terminal. Alternatively, the base station may signal to the terminal each of information indicating the aggregation factor indicating the number of aggregated slots excluding the dropped slots and information indicating the number of transmitted PUSCH instances excluding the dropped PUSCH instances. That is, each of the nominal aggregation factor and the number of transmitted PUSCH instances may be 2, and this may coincide with the number of PUSCH instances that the terminal actually transmits.

In the case of a configured grant-based PUSCH, the terminal may count the number of aggregated slots including slots dropped within one period, and count the number of transmitted PUSCH instances including PUSCH instances dropped within one period. Alternatively, the terminal may count the number of aggregated slots excluding the slots dropped within one period, and count the number of transmitted PUSCH instances excluding the PUSCH instance dropped within one period.

Meanwhile, when a PUSCH is repeatedly transmitted, a partial resource region of a specific PUSCH instance may not be used for transmission. For example, a partial resource region (e.g., some symbols) of a specific PUSCH instance may be configured as a rate matching resource region, and the terminal may not map the PUSCH to the partial resource region. Alternatively, UCI may be piggybacked on the specific PUSCH instance. In this case, the size of a resource to which UL-SCH data is mapped in the specific PUSCH instance may be reduced. In the above-described cases, transmission of the PUSCH instance may not help to guarantee the PUSCH transmission reliability.

Accordingly, as another method of dropping some slots or some PUSCH instances, when a size of a resource to which UL-SCH data and/or UCI is mapped for a specific PUSCH instance is equal to or less than a reference value (hereinafter, referred to as '$N_{sch}$'), the terminal may omit transmission of the corresponding PUSCH instance. This may be referred to as 'Method 210'. The size of the resource may be the number of REs to which UL-SCH data and/or UCI is mapped. $N_{sch}$ may be predefined in the specification. Alternatively, the base station may configure $N_{sch}$, and may inform the terminal of the configured $N_{sch}$. For example, $N_{sch}$ may be set (e.g., defined) to 0.

Method 211, which is similar to Method 210, may be defined. In Method 211, when an effective code rate of UL-SCH data and/or UCI is higher than a reference value for a certain PUSCH instance, the terminal may drop transmission of the corresponding PUSCH instance. The effective code rate may be determined by the total number of REs to which UL-SCH data and/or UCI is mapped. In Method 211, the reference value may be predefined in the specification. Alternatively, the base station may set the reference value used in Method 211, and may inform the terminal of the set reference value.

The above-described resource allocation methods (e.g., Method 110 and Method 120) may be used in combination with Method 210 or Method 211. In the exemplary embodiment shown in FIG. 9B, the PUSCH may be repeatedly transmitted in the slot n and the slot n+2. For example, when the PUSCH is scheduled to the terminal by Method 110, a resource region (e.g., symbol position and/or duration) of the PUSCH instance in the slot n+1 may be implicitly determined. In this case, the terminal may determine whether to transmit the corresponding PUSCH instance by using Method 210 or Method 211. In the exemplary embodiment shown in FIG. 9B, the transmission of the PUSCH instance in the slot n+1 may be dropped.

For another example, when the PUSCH is scheduled to the terminal by Method 120 to Method 123, the base station may signal an SLIV for the PUSCH instance of the slot n and an SLIV for the PUSCH instance of the slot n+2 to the terminal. In this case, there is a need for a method for the terminal to identify that a PUSCH instance is not allocated in the slot n+1. To this end, the base station may signal information on a slot or PUSCH instance corresponding to each SLIV to the terminal. Alternatively, the base station may transmit the SLIV for the dropped slot or the dropped PUSCH instance, and the corresponding SLIV may be set to NULL or a value corresponding to NULL.

When the SLIV received from the base station is NULL or a value corresponding to NULL, the terminal may omit the transmission of the slot or PUSCH instance corresponding to the SLIV. In the exemplary embodiment shown in FIG. 9B, the base station may transmit three SLIVs to the terminal for the slot n to the slot n+2. Here, the SLIV for the slot n+1 may be set to NULL. The above-described methods may be applied even when a PUSCH is not repeatedly transmitted (e.g., when a single PUSCH is transmitted in a single slot).

Even when transmissions of some PUSCH instances are dropped, the RVs applied to the respective PUSCH instances constituting repetitive transmission may not be changed. For example, it may be assumed that the RV pattern is (0, 2, 3, 1), and three PUSCH instances are scheduled for PUSCH repetitive transmission. In this case, "when the PUSCH is a configured grant-based PUSCH" or "when a DCI indicating that the RV applied to the PUSCH is 0" is received, the RVs applied to the first, second, and third PUSCH instances may be 0, 2, and 3, respectively. Even when transmission of the second PUSCH instance is dropped, the RVs applied to the first and third PUSCH instances may be 0 and 3, respectively, without change.

Alternatively, when the transmissions of some PUSCH instances are dropped, the RV(s) of the PUSCH instance (s) after the dropped PUSCH instance may be changed. When the RVs applied to the first, second, and third PUSCH instances are 0, 2, and 3, respectively, and the transmission of the second PUSCH instance is dropped, the RV applied to the third PUSCH instance may be changed from 3 to 2. That is, the RV pattern may be applied to PUSCH instances that are actually transmitted without being dropped.

The above-described method may also be applied to downlink communication. When the PDSCH is scheduled to be repeatedly transmitted, the terminal may omit a reception operation for a specific slot or PDSCH instance when a certain criterion is satisfied. The terminal may assume that the PDSCH instance omitted in the reception procedure is not transmitted from the base station. In this case, the terminal may receive another signal and/or channel in the resource region of the PDSCH instance omitted in the reception procedure. The criterion for omitting transmission and reception of the specific PDSCH instance may be the same as or similar to the criterion for omitting transmission and reception of the above-described PUSCH instance. The above-described method may be applied even when the PDSCH is not repeatedly transmitted (e.g., when a single PDSCH is transmitted in a single slot).

[Method for Transmitting PUSCH in Downlink Symbols]

In general, the terminal cannot transmit a PUSCH in a symbol designated as a downlink symbol by slot format configuration. The slot format configuration may include semi-static slot format configuration and dynamic slot format configuration by SFI. However, in order to satisfy transmission reliability and latency requirements in the communication system supporting URLLC services, the terminal may transmit a PUSCH in downlink symbols. For example, when a PUSCH resource region scheduled by the base station includes downlink symbols, the terminal may transmit the PUSCH in the corresponding downlink symbols. In addition, when a PDSCH resource region scheduled by the base station includes uplink symbols, the terminal may receive the PDSCH in the corresponding uplink symbols. This may be referred to as 'Method 300'.

The downlink symbols used for the PUSCH transmission may be downlink symbols indicated by slot format configuration information received at the terminal before the reception of the DCI (e.g., uplink grant) including the scheduling information of the PUSCH. The downlink symbols used for the PUSCH transmission may be symbols overridden to be downlink symbols by an SFI after being configured as flexible symbols by a semi-static slot format configuration. That is, even when a specific symbol is configured as a downlink symbol, the base station may improve the URLLC transmission performance by scheduling the downlink symbol to be used for uplink URLLC transmission.

Information indicating whether Method 300 is applied may be signaled from the base station to the terminal. For example, information indicating whether Method 300 is applied may be included in a DCI. In this case, the information indicating whether to apply Method 300 may be included in an existing field of the DCI or may be represented by a separate indicator (e.g., an indicator of 1 bit). In uplink communication, the DCI may be an uplink grant scheduling a PUSCH, and in downlink communication, the DCI may be a DCI scheduling a PDSCH. The DCI including information indicating whether Method 300 is applied may follow a specific DCI format.

For example, in the NR communication system, a DCI including information indicating whether Method 300 is applied may follow a new DCI format having a payload size smaller than those of the existing DCI formats 0_0 and 1_0. For another example, the DCI including information indicating whether to apply Method 300 may be a DCI with a CRC scrambled by a specific RNTI. The specific RNTI may be an RNTI determined by the methods described above. A PUSCH scheduled by a 'DCI conforming to the new DCI format' or a 'DCI with a CRC scrambled by a specific RNTI' may be transmitted in downlink symbols. That is, the terminal may expect that a resource region allocated for the PUSCH includes downlink symbols, and may transmit the PUSCH in a resource region scheduled by the base station regardless of whether the resource region allocated for the PUSCH includes downlink symbols.

As a different method from Method 300, the base station may override a symbol previously configured as a downlink symbol to a flexible symbol or an uplink symbol through an SFI. When the transmission direction of the same symbol is indicated differently by a plurality of SFIs, the terminal may apply the most recent SFI to the corresponding symbol. When the SFI is received before or at the same time as the reception time of the uplink grant for the URLLC PUSCH, the terminal may transmit the PUSCH in the symbols overridden as flexible or uplink symbols by the corresponding SFI.

[Frequency Hopping Method and Multi-Beam Transmission Method]

Frequency hopping and multi-beam transmission may be applied to PUSCH repetitive transmission to obtain frequency and spatial diversity. In the NR communication system, frequency hopping for PUSCH may be used with a resource allocation type 1. The resource allocation type 1 may be a method of scheduling a frequency resource region to which a PUSCH is allocated based on a start virtual resource block (VRB) and the number of consecutive VRBs. "When a frequency hopping field included in the DCI indicates that frequency hopping is applied' or 'when frequency hopping is configured to be applied by RRC signaling for configured grant-based transmission', the terminal may transmit the PUSCH according to frequency hopping.

In the above-described method, frequency hopping may be applied between a plurality of PUSCH instances. For example, when the number of frequency regions (hereinafter, referred to as 'hops') used for the frequency hopping is defined as $N_f$, the terminal may transmit a k-th PUSCH instance on a mod (k, $N_f$)-th hop. Each of $N_f$ and k may be a natural number. When $N_f$ is 2, the terminal may transmit an odd PUSCH instance in the first hop and may transmit an even PUSCH instance in the second hop. Even when some PUSCH instances are dropped by the above-described method, the hops in which the remaining PUSCH instances are transmitted may be maintained without change. The offset between the frequency regions occupied by the respective hops may be represented by the number of RBs, and the offset may be signaled from the base station to the terminal.

In the above-described method, frequency hopping may be applied within one PUSCH instance. For example, when the number of symbols to which the k-th PUSCH instance is allocated is $N_{symb,k}$ and $N_f$ is 2, the first floor ($N_{symb,k}/2$) symbols of the PUSCH instance may be transmitted in the first hop, and the remaining ($N_{symb,k}$−floor ($N_{symb,k}/2$)) symbols of the PUSCH instance may be transmitted in the second hop. Here, $N_{symb,k}$ may be a natural number. According to the above-described method, since $N_{symb,k}$ may be different for each PUSCH instance, the number of symbols allocated to each frequency hop may also be different for each PUSCH instance.

The frequency hopping within a PUSCH instance may be applied to all PUSCH instances. Alternatively, frequency hopping within a PUSCH instance may be selectively applied to some PUSCH instances. For example, the frequency hopping may be applied to PUSCH instance(s) having a number of symbols ($N_{symb,k}$) equal to or greater than a reference value, and the terminal may transmit the PUSCH instance(s) having a number of symbols ($N_{symb,k}$) less than the reference value in a single frequency hop. The single frequency hop may be the first hop. For example, the reference value for $N_{symb,k}$ may be 2. Meanwhile, the PUSCH data may not be mapped to symbols to which a DM-RS for decoding the PUSCH is mapped. In this case, the reference value for $N_{symb,k}$ may be four.

The frequency hopping may be performed in one BWP. For example, the frequency hopping may be performed in the active uplink BWP. The frequency hopping may also be applied to a plurality of active BWPs (e.g., a plurality of active uplink BWPs). The plurality of active BWPs may be BWPs configured within one carrier. Alternatively, the plurality of active BWPs may be BWPs configured in different carriers. In this case, the base station may inform the terminal of the ID of the BWP corresponding to each frequency hop and the frequency position (e.g., the position of the start RB) within the BWP. In addition, the base station may inform the terminal of the ID of the carrier corresponding to each frequency hop.

A plurality of transmission beams and/or precoders may be used for PUSCH transmission. For example, different transmission beams and/or precoders may be applied to a plurality of PUSCH instances. For example, when the number of transmission beams and/or precoders is $N_b$, the terminal may transmit a k-th PUSCH instance using a mod (k, $N_b$)-th transmission beam and/or precoder. Here, each of $N_b$ and k may be a natural number. Even when some PUSCH instances are dropped by the above-described method, the transmission beam and/or precoder applied to the remaining PUSCH instances may be maintained without change.

A plurality of transmission beams and/or precoders may be used for transmission of one PUSCH instance. A set of symbols to which each transmission beam and/or precoder is applied may be determined in the same or similar manner to the frequency hopping method described above. For example, when the number of symbols to which the k-th PUSCH instance is allocated is $N_{symb,k}$ and $N_b$ is 2, the first transmission beam and/or precoder may be applied to transmit the first floor ($N_{symb,k}/2$) symbols of the PUSCH instance, and the second transmission beam and/or precoder may be applied to transmit the remaining ($N_{symb,k}$−floor ($N_{symb,k}/2$)) symbols of the PUSCH instance. This method may be applied to all PUSCH instances constituting PUSCH repetitive transmission. Alternatively, this method may be applied to some PUSCH instance(s) that meet a certain condition.

In uplink communication, the base station may inform the terminal of the transmission beam and/or precoder by indicating (e.g., configuring) an SRS resource indicator (SRI), a transmit precoding matrix indicator (TPMI), and/or a transmission rank. The terminal may transmit the PUSCH instance and the DM-RS for decoding the corresponding PUSCH instance using the same antenna port(s) as the antenna port(s) of the SRS resource indicated by the SRI.

In downlink communication, the transmission beam may correspond to a QCL that the terminal assumes for reception of the PDSCH. The QCL may include various types or parameters, including a spatial QCL (e.g., QCL-TypeD, spatial Rx parameter). QCL source information (e.g., a set of antenna port(s) for which the terminal can assume the same QCL as the DM-RS of the data channel instance) for reception of a data channel instance may be predefined in the specification. Alternatively, the QCL source information for receiving the data channel instance may be signaled from the base station to the terminal. The QCL source information may be included in TCI state information transmitted through signaling, and the signaling procedure may be performed through a combination of one or more of RRC signaling, MAC CE, and DCI.

The frequency hopping method may be used in combination with a method of applying multiple beams and/or multiple precoders. In addition, the frequency hopping method and the method of applying multiple beams and/or multiple precoders may be applied to other resource allocation methods in addition to the PUSCH and PDSCH resource allocation methods described above. Although the above-described exemplary embodiments have been described as being applied to the PUSCH, the same or similar exemplary embodiments may be applied to other data channels (e.g., PDSCH and PSSCH) as well as the PUSCH.

The embodiments of the present disclosure may be implemented as program instructions executable by a variety of computers and recorded on a computer readable medium. The computer readable medium may include a program instruction, a data file, a data structure, or a combination thereof. The program instructions recorded on the computer readable medium may be designed and configured specifically for the present disclosure or can be publicly known and available to those who are skilled in the field of computer software.

Examples of the computer readable medium may include a hardware device such as ROM, RAM, and flash memory, which are specifically configured to store and execute the program instructions. Examples of the program instructions include machine codes made by, for example, a compiler, as well as high-level language codes executable by a computer, using an interpreter. The above exemplary hardware device can be configured to operate as at least one software module in order to perform the embodiments of the present disclosure, and vice versa.

While the embodiments of the present disclosure and their advantages have been described in detail, it should be understood that various changes, substitutions and alterations may be made herein without departing from the scope of the present disclosure.

What is claimed is:
1. A method of a terminal, the method comprising:
  receiving downlink control information (DCI) including resource allocation information of a physical uplink shared channel (PUSCH) from a base station;
  determining a time resource region of the PUSCH based on the resource allocation information;
  identifying a plurality of valid symbol sets included in the time resource region; and
  transmitting each of a plurality of PUSCH instances associated with the PUSCH in each of the plurality of valid symbol sets to the base station, wherein the each of the plurality of valid symbol sets includes one or more consecutive symbols in one slot, there is at least one symbol that does not belong to the plurality of valid symbol sets between the plurality of valid symbol sets, the one or more consecutive symbols included in the each of the plurality of valid symbol sets are symbol(s) except for downlink symbol(s) semi-statically configured by the base station, the one or more consecutive symbols included in the each of the plurality of valid symbol sets are symbol(s) after N symbol(s) from a last symbol of downlink symbol(s) semi-statically configured by the base station, and N is a natural number and is configured with the terminal by a radio resource control (RRC) signaling procedure.

2. The method of claim 1, wherein a frequency domain resource region of the plurality of PUSCH instances is identical to a frequency domain resource region of the PUSCH.

3. The method of claim 1, wherein a location of a symbol in which a demodulation reference signal (DM-RS) for the PUSCH is mapped is determined based on a first mapping type.

4. The method of claim 1, wherein, when a number of symbols included in a first valid symbol set of the plurality of valid symbol sets is less than a threshold, a first PUSCH instance corresponding to the first valid symbol set is not transmitted.

5. The method of claim 1, wherein, when transmission of one or more PUSCH instances of the plurality of PUSCH instances is dropped, a redundancy version (RV) applied to each of remaining PUSCH instances of the plurality of PUSCH instances is not changed.

6. The method of claim 1, wherein the N symbol(s) is used for switching from a downlink communication to an uplink communication.

7. A method of a base station, the method comprising:
transmitting downlink control information (DCI) including resource allocation information of a physical uplink shared channel (PUSCH) to a terminal;
identifying a plurality of valid symbol sets included in a time resource region of the PUSCH which is determined based on the resource allocation information; and
receiving each of a plurality of PUSCH instances associated with the PUSCH in each of the plurality of valid symbol sets from the terminal,
wherein the each of the plurality of valid symbol sets includes one or more consecutive symbols in one slot, there is at least one symbol that does not belong to the plurality of valid symbol sets between the plurality of valid symbol sets, the one or more consecutive symbols included in the each of the plurality of valid symbol sets are symbol(s) except for downlink symbol(s) semi-statically configured by the base station, the one or more consecutive symbols included in the each of the plurality of valid symbol sets are symbol(s) after N symbol(s) from a last symbol of downlink symbol(s) semi-statically configured by the base station, and N is a natural number and is configured with the terminal by a radio resource control (RRC) signaling procedure.

8. The method of claim 7, wherein a frequency domain resource region of the plurality of PUSCH instances is identical to a frequency domain resource region of the PUSCH.

9. The method of claim 7, wherein a location of a symbol in which a demodulation reference signal (DM-RS) for the PUSCH is mapped is determined based on a first mapping type.

10. The method of claim 7, wherein, when a number of symbols included in a first valid symbol set of the plurality of valid symbol sets is less than a threshold, a first PUSCH instance corresponding to the first valid symbol set is not transmitted.

11. The method of claim 7, wherein, when transmission of one or more PUSCH instances of the plurality of PUSCH instances is dropped, a redundancy version (RV) applied to each of remaining PUSCH instances of the plurality of PUSCH instances is not changed.

12. The method of claim 7, wherein the N symbol(s) is used for switching from a downlink communication to an uplink communication.

\* \* \* \* \*